US012152087B2

(12) United States Patent
Lehmann

(10) Patent No.: US 12,152,087 B2
(45) Date of Patent: Nov. 26, 2024

(54) DEUTERATED MELFLUFEN COMPOUNDS

(71) Applicant: Oncopeptides AB, Stockholm (SE)

(72) Inventor: Fredrik Lehmann, Knivsta (SE)

(73) Assignee: Oncopeptides Innovation AB, Stockholm (SE)

( * ) Notice: Subject to any disclaimer, the term of this patent is extended or adjusted under 35 U.S.C. 154(b) by 769 days.

(21) Appl. No.: 17/286,002

(22) PCT Filed: Oct. 17, 2019

(86) PCT No.: PCT/EP2019/078250
§ 371 (c)(1),
(2) Date: Apr. 16, 2021

(87) PCT Pub. No.: WO2020/079165
PCT Pub. Date: Apr. 23, 2020

(65) Prior Publication Data
US 2021/0388024 A1   Dec. 16, 2021

(30) Foreign Application Priority Data

Oct. 18, 2018   (GB) ..................... 1816998
Jul. 5, 2019    (GB) ..................... 1909695

(51) Int. Cl.
*C07K 5/06*     (2006.01)
*A61K 45/06*    (2006.01)
(Continued)

(52) U.S. Cl.
CPC .......... *C07K 5/06191* (2013.01); *A61K 45/06* (2013.01); *A61P 35/00* (2018.01);
(Continued)

(58) Field of Classification Search
CPC ..... C07K 5/06191; A61K 45/06; A61P 35/00; A61P 35/02; C07F 13/00; C07B 2200/05
See application file for complete search history.

(56) References Cited

FOREIGN PATENT DOCUMENTS

CN     104725380 A     6/2015
WO     2001/096367 A1  12/2001
(Continued)

OTHER PUBLICATIONS

Pallante, S. L., et al. "Quantitation by Gas Chromatography-Chemical Ionization-Mass Spectrometry of Phenylalanine Mustard in Plasma of Patients." Cancer Research, vol. 40, No. 7, Jul. 1980, pp. 2268-2272. (Year: 1980).*
(Continued)

*Primary Examiner* — Valerie Rodriguez-Garcia
*Assistant Examiner* — Kyle Nottingham
(74) *Attorney, Agent, or Firm* — Biospark Intellectual Property Law

(57) ABSTRACT

The invention provides a compound of formula (I), or a pharmaceutically acceptable salt thereof (Formula I), wherein, each $R^1$-$R^{30}$ is independently selected from the group consisting of H and deuterium, and at least one of
(Continued)

$R^1$-$R^{30}$ is deuterium with an abundance level greater than the naturally occurring abundance of deuterium. The invention also provides pharmaceutical compositions containing the compounds, and uses of the compounds.

(I)

17 Claims, 8 Drawing Sheets

(51) Int. Cl.
*A61P 35/00* (2006.01)
*A61P 35/02* (2006.01)
*C07F 13/00* (2006.01)
(52) U.S. Cl.
CPC .............. *A61P 35/02* (2018.01); *C07F 13/00* (2013.01); *C07B 2200/05* (2013.01)

(56) References Cited

FOREIGN PATENT DOCUMENTS

| WO | 2010/044981 | A2 | | 4/2010 | |
|---|---|---|---|---|---|
| WO | 2011/153157 | A2 | | 12/2011 | |
| WO | 2012/146625 | A1 | | 11/2012 | |
| WO | 2014/047167 | A1 | | 3/2014 | |
| WO | 2014/065751 | A1 | | 5/2014 | |
| WO | 2014/120654 | A1 | | 8/2014 | |
| WO | 2015/084622 | A1 | | 6/2015 | |
| WO | 2016/144901 | A1 | | 9/2016 | |
| WO | 2016/180740 | A1 | | 11/2016 | |
| WO | WO-2017093443 | A1 | * | 6/2017 | ........... A61K 31/216 |

OTHER PUBLICATIONS

Carlier, Charlotte, et al. "Preclinical Activity of Melflufen (J1) in Ovarian Cancer." Oncotarget, vol. 7, No. 37, Aug. 2016, p. 59322-35. PubMed Central, https://doi.org/10.18632/oncotarget.11163. (Year: 2016).*
Berglund et al., 2015, "First-in-human, phase I/IIa clinical study of the peptidase potentiated alkylator melflufen administered every three weeks to patients with advanced solid tumor malignancies" Invest. New Drugs, 33(6): 1232-1241.
Carlier et al., 2016, "Preclinical activity of melflufen (J1) in ovarian cancer" Oncotarget, 7(37): 59322-59335.
Fisher et al., 2006, "The complexities inherent in attempts to decrease drug clearance by blocking sites of CYP-mediated metabolism" Curr. Opin. Drug Discov. Devel., 9(1): 101-109.
Gullbo et al., 2003, "Activity of Hydrolytic Enzymes in Tumour Cells is a Determinant for Anti-tumor Efficacy of the Melphalan Containing Prodrug J1" J. Drug Target., 11: 355-363.
Larsson et al., 1992, "Laboratory Determination of Chemotherapeutic Drug Resistance in Tumor Cells from Patients with Leukemia, Using a Fluorometric Microculture Cytotoxicity Assay (FMCA)" Int. J. Cancer, 50: 177-185.
Tung, 2010, "The Development of Deuterium-Containing Drugs" Innovations Pharm. Technol., 32: 24-26.
Wickstrom et al., 2008, "The novel alkylating prodrug J1: diagnosis directed activity profile ex vivo and combination analyses in vitro" Invest. New Drugs, 26: 195-204.
Wickstrom et al., 2010, "The alkylating prodrug J1 can be activated by aminopeptidase N, leading to a possible target directed release of melphalan" Biochem. Pharmacol., 79: 1281-1290.
Benchekroun et al., 1997, "Deuterium isotope effects on caffeine metabolism," Eur. J. Drug Metab. Pharmacokinet, 22:127-133.
Declaration by R. Tung filed Nov. 6, 2010 in the file history of U.S. Pat. No. 7,932,235.
Drake et al., 2018, "Deuterium kinetic isotope effect studies of a potential in vivo metabolic trapping agent for Monoamine Oxidase-B," ACS Chem Neurosci 9(12):3024-3027.
Liu 2016, "Deuterated Drugs Progress," Chemical Design Newsletter 42(4):199-200.
Manley et al., 2013, "The kinetic deuterium isotope effect as applied to metabolic deactivation of imatinib to the des-methyl metabolite, CGP74588," Bioorganic & Medicinal Chemistry 21:3231-3239.
Schneider et al., 2006, "Enhanced Plasma Concentration by Selective Deuteration of Rofecoxib in Rats," Arzneim Forsch, 56:295-300.
Tung, 2010, "The Development of Deuterium-Containing Drugs," Innovations Pharm. Technol. 32:24-28.
Harbeson and Tung, 2014, "Deuterium Medicinal Chemistry: A New Approach to Drug Discovery and Development," MedChem News 2:8-22.

* cited by examiner

DEUTERATED MELFLUFEN COMPOUNDS

FIELD OF THE INVENTION

The present invention relates to novel deuterated melflufen derivatives with especially beneficial properties. The novel deuterated melflufen derivatives, or salts thereof, find use in the treatment or prophylaxis of cancer.

BACKGROUND OF THE INVENTION

Melflufen (also known as melphalan flufenamide and L-Melphalanyl-4-fluoro-L-phenylalanine ethyl ester), is an anti-tumour agent useful in the treatment cancer, particularly the treatment of multiple myeloma. Melflufen is described in WO 01/96367 and WO 2014/065751. The structure of the hydrochloride salt of melflufen is shown below:

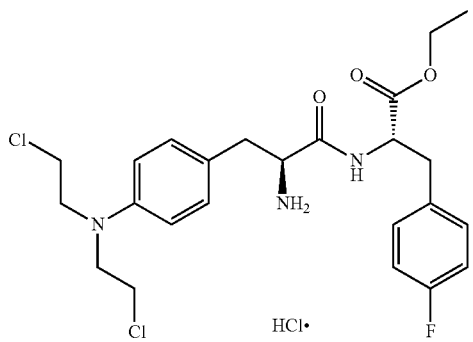

Melflufen is a potent and highly lipophilic alkylating agent and it achieves targeted delivery of alkylating metabolites to tumour cells. In contrast to other alkylating agents that are hydrophilic, the high lipophilicity of melflufen leads to its rapid uptake into tissues and cells. Once inside a cell melflufen may bind directly to DNA or it may be readily hydrolysed by intracellular peptidases into melphalan or hydrolysed by intracellular esterases into des-ethylmethfulfen, which also has alkylating properties. The high activity of esterases and peptidases in human tumours leads to the rapid formation of melflufen's metabolites in these cells which then leads to inflow of more melflufen (Gullbo, J., et al, J Drug Target, (2003) Vol 11, pages 355-363; Wickstrom, M., et al, Biochem Pharmacol (2010) Vol 79, pages 2381-1290). Since des-ethylmelflufen and melphalan are relatively hydrophilic, there is a possibility for intracellular trapping of these agents.

The addition of melflufen to panels of primary cultures of human tumour cells, results in a similar pattern of activity to that of melphalan, but with 50 to 100 fold higher efficacy (Wickstrom, M., et al, Invest New Drugs (2008) Vol 26, pages 195-204), which is explained by the 10 to 20 fold higher intracellular concentration (Gullbo, J., et al, J Drug Target, (2003) Vol 11, pages 355-363; Wickstrom, M., et al, Biochem Pharmacol (2010) Vol 79, pages 2381-1290). This may be explained by the highly efficient uptake of melflufen into these cells and efficient formation of the melflufen metabolites.

Melflufen is generally provided in crystalline form after synthesis. The crystalline form can only be dissolved in highly acidic aqueous solutions that are often unsuitable for manufacturing and pharmaceutical purposes. In previous pharmaceutical preparations, the crystalline form was dissolved in a dimethylacetamide (DMA) and glucose solution. However, this preparation was unstable and readily formed unwanted melflufen dimers. Organic solvents, such as DMA, can also be hazardous to patients and can damage medical devices used for administration. As described in WO 2012/146625 and WO 2014/065751, lyophilised preparations of melflufen have been found to have improved stability and solubility in aqueous solutions.

Compounds that are inherently unstable are difficult to handle and are more likely to form unwanted metabolites and impurities. Alkylating agents, such as melflufen, present further difficulties as they have the potential to form unwanted genotoxic metabolites and impurities that may cause off-target effects in a patient. Therefore, alkylating agents with poor stability are often difficult to handle and may have undesirable pharmacological properties. There is therefore a need for melflufen derivatives with improved stability and handling properties.

The present inventors have discovered that deuterated derivatives of melflufen have improved properties compared to melflufen with a natural abundance level of deuterium.

SUMMARY OF THE INVENTION

The present invention provides a compound of formula (I), or a pharmaceutically acceptable salt thereof,

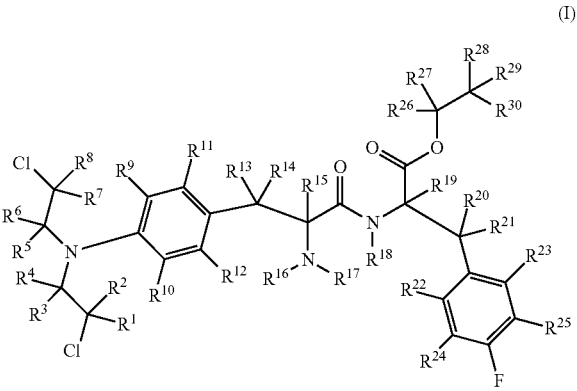

wherein,
each $R^1$-$R^{30}$ is independently selected from the group consisting of H and deuterium, and at least one of $R^1$-$R^{30}$ is deuterium with an abundance level greater than the naturally occurring abundance of deuterium.

The present invention further provides a compound of formula (Ia), or a pharmaceutically acceptable salt thereof,

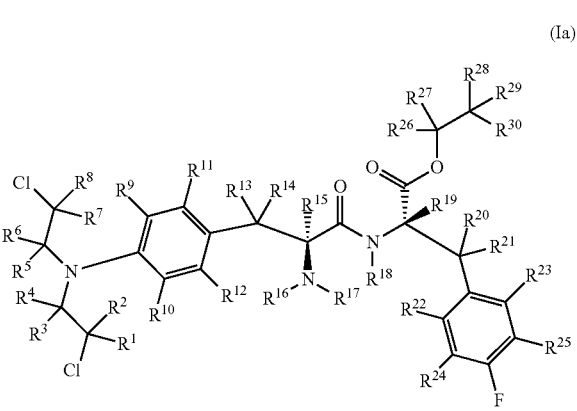

wherein, each $R^1$-$R^{30}$ is independently selected from the group consisting of H and deuterium, and at least one of $R^1$-$R^{30}$ is deuterium with an abundance level greater than the naturally occurring abundance of deuterium.

The invention further provides a composition comprising a deuterated melflufen of formula (I) or (Ia), together with an acceptable carrier. The composition may optionally comprise an additional therapeutic agent, for example a protease inhibitor (PI), an immunomodulatory drug (IMiD) or an alkylator.

The invention further provides a pharmaceutical composition comprising a deuterated melflufen of formula (I) or (Ia), together with a pharmaceutically acceptable carrier. The pharmaceutical composition may optionally comprise an additional therapeutic agent, for example a protease inhibitor (PI), an immunomodulatory drug (IMiD) or an alkylator.

The invention further provides a compound or a pharmaceutical composition according to the invention for use as a medicament. Further, there is also provided a compound or a pharmaceutical composition according to the invention for use in the treatment or prophylaxis of cancer, for example multiple myeloma, breast cancer, lung cancer, ovarian cancer, leukaemias and lymphomas.

The invention further provides a method of treating a patient which comprises administering a pharmaceutically effective amount of a compound or pharmaceutical composition according to the invention.

DETAILED DESCRIPTION OF THE INVENTION

Figure 1:
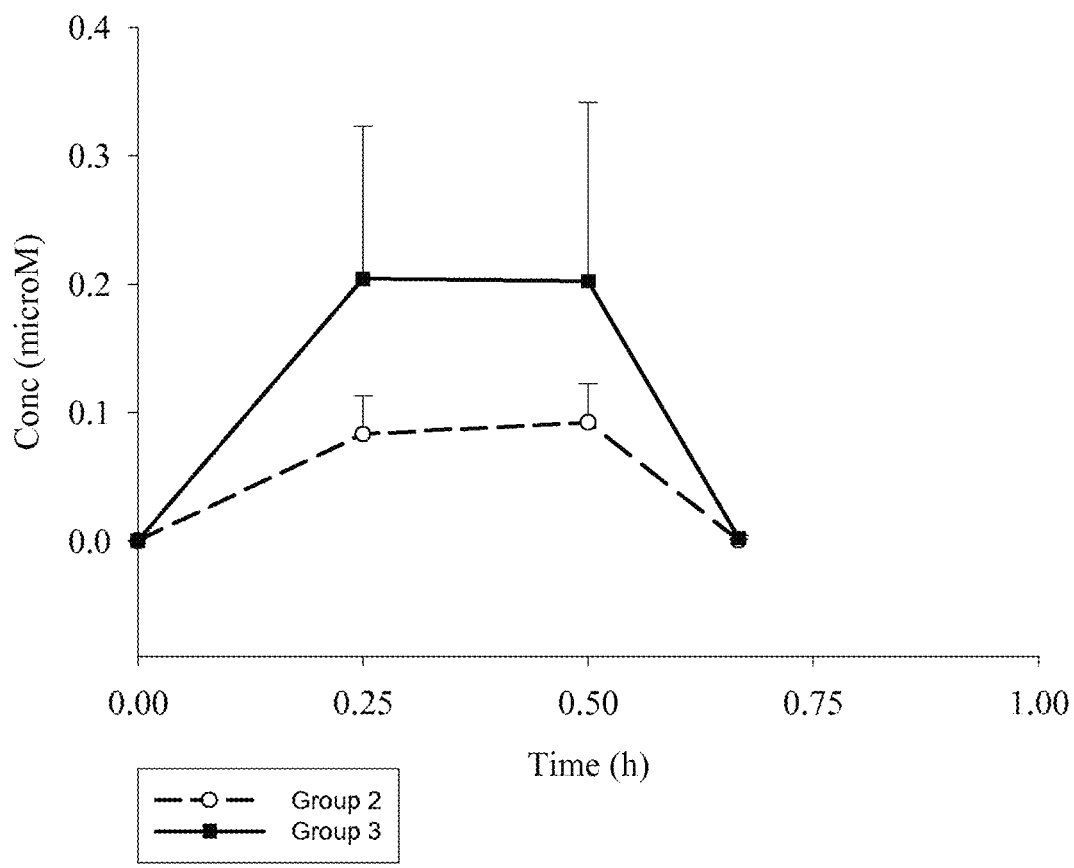
FIG. 1 shows the mean plasma concentrations of melflufen-d5 (III) in combined male and female beagle dogs after 1.25 and 2.5 mg/kg infusion of melflufen-d5 (III).

The present invention provides a compound of formula (I), or a pharmaceutically acceptable salt thereof, wherein each $R^1$-$R^{30}$ is independently selected from the group consisting of H and deuterium, and at least one of $R^1$-$R^{30}$ is deuterium with an abundance level greater than the naturally occurring abundance of deuterium.

The present invention further provides a compound of formula (Ia), or a pharmaceutically acceptable salt thereof, wherein each $R^1$-$R^{30}$ is independently selected from the group consisting of H and deuterium, and at least one of $R^1$-$R^{30}$ is deuterium with an abundance level greater than the naturally occurring abundance of deuterium.

The naturally occurring abundance of deuterium is 0.0156 mol %, wherein mol % is the percentage of the total moles of a sample's hydrogen that is deuterium. Therefore, in 1 mole of naturally occurring hydrogen 0.156 mmol is deuterium, or in a sample of $6.022 \times 10^{23}$ naturally occurring hydrogen atoms there are $9.39 \times 10^{19}$ atoms of deuterium, or in a sample of 6413 naturally occurring hydrogen atoms there is one atom of deuterium.

There are 30 carbon-hydrogen (C—H) groups in melflufen and each contains a naturally occurring distribution of hydrogen isotopes. Therefore, in a sample of melflufen, the abundance of deuterium at each position is approximately 0.0156 mol %. Therefore, in 1 mole of melflufen there is 4.68 mmol of deuterium, or in a sample of $6.022 \times 10^{23}$ molecules of melflufen there is $2.82 \times 10^{21}$ atoms of deuterium, or in 214 molecules of melflufen there is 1 atom of deuterium.

Where one or more of $R^1$-$R^{30}$ of formula (I) or (Ia) are indicated herein to be "deuterium", the deuterium abundance at the indicated position is greater than the naturally occurring abundance of deuterium. A deuterium abundance level greater than the naturally occurring abundance of deuterium may be at least 1 mol %, 5 mol %, 10 mol %, 50 mol %, 90 mol % or 98 mol % deuterium.

Deuterium is a safe and stable isotope of hydrogen. The energy required to break a carbon-deuterium (C-D) bond is higher than that required to break a carbon-hydrogen (C—H) bond. Therefore, reactions that involve the breaking of a C-D bond progress at a slower rate than reactions that break a C—H bond. If the C—H bond is broken in a rate-determining step of a reaction, then substitution to a C-D bond will decrease the reaction rate. This effect is called the Deuterium Kinetic Isotope Effect (DKIE).

The influence of deuteration on the pharmacological properties of a drug is unpredictable and must be determined empirically. In some select cases, deuteration has been shown to improve the pharmacological properties of a drug (see for example WO 2010/044981). In other cases, deuteration may have no clinically relevant effect or may have a negative effect on the pharmacological properties of a drug.

Deuteration of a drug may decrease the rate at which it is metabolised by enzymes such as such as Cytochromes P450 (CYPs), esterases, peptidases, reductases, dehydrogenases and oxidases, thus altering its pharmacological properties. It is also possible that deuteration may have the effect of altering the metabolic profile of drug, a phenomenon which is often referred to as "metabolic switching".

Metabolic switching can occur when a deuterated drug binds to metabolising enzymes in a different conformation compared to the non-deuterated drug. This can lead to the formation of different proportions of known metabolites or even the formation of new metabolites (Fischer et al., Curr Opin Drug Discov Devel, 2006, 9(1), 100-109). It is not possible to predict how an increased abundance of deuterium at a particular position may alter the metabolite profile of a drug. Nor is it possible to predict if an altered metabolite profile will improve, or be detrimental to, the pharmacological properties of a drug.

The inventors of the present invention have surprisingly found that deuterated melflufen derivatives according to the invention have particularly beneficial properties. For example, deuterated melflufen derivatives when administered by infusion result in increased systemic exposure to the derivative itself, as well as the active metabolite melphalan, compared to an equivalent dose of melflufen. This effect is shown in Example (a) below, and in particular in FIGS. 3, 4, 9 and 10 of Example (a) which show the mean and individual $C_{max}$ and $AUC_{last}$ melflufen-d5 (III)/melflufen or melphalan after administration of melflufen-d5 (III) or melflufen to dogs.

The result of increased exposure to melflufen-d5 (III) and melphalan for identical doses of melflufen-d5 (III) and melflufen has very significant benefits. As mentioned above, the excellent clinical efficacy of melflufen may be explained by the highly efficient uptake of melflufen into cells and efficient formation of the melflufen metabolites. Thus, a derivative that leads to even higher exposure of the melflufen derivative, and higher exposure of the active metabolite melphalan, compared to melflufen is especially advantageous as it is expected to improve both of those properties of melflufen. In addition to those advantages meaning that less compound is needed to be made, stored and administered, it also allows for a lower dose of the deuterated melflufen derivative to be administered compared to the equivalent dose of melflufen, which reduces the risk of side-effects from administration of melflufen; or, if the same dose as a dose of melflufen is administered, a higher exposure to the deuterated melflufen derivative and melphalan can be achieved, leading to a better chance of providing a clinical benefit for a patient without increasing the risk of intolerable toxic side effects.

Preferred compounds according to the invention are those wherein at least one of $R^1$-$R^{30}$ is deuterium. Particularly preferred compounds according to the invention are those wherein at least one of $R^1$-$R^8$ is deuterium; at least one of $R^9$-$R^{15}$ is deuterium; at least one of $R^{16}$-$R^{18}$ is deuterium; at least one of $R^{19}$-$R^{25}$ is deuterium; or at least one of $R^{26}$-$R^{30}$ is deuterium.

Further preferred compounds according to the invention are those wherein, at least two of $R^1$-$R^8$ are deuterium; at least three of $R^1$-$R^8$ are deuterium; at least four of $R^1$-$R^8$ are deuterium; at least five of $R^1$-$R^8$ are deuterium; at least six of $R^1$-$R^8$ are deuterium; at least seven of $R^1$-$R^8$ are deuterium; or at least eight of $R^1$-$R^8$ are deuterium.

Further preferred compounds according to the invention are those wherein, at least two of $R^9$-$R^{15}$ are deuterium; at least three of $R^9$-$R^{15}$ are deuterium; at least four of $R^9$-$R^{15}$ are deuterium; at least five of $R^9$-$R^{15}$ are deuterium; at least six of $R^9$-$R^{15}$ are deuterium; or at least seven of $R^9$-$R^{15}$ are deuterium.

Further preferred compounds according to the invention are those wherein, at least two of $R^{16}$-$R^{18}$ are deuterium; or at least three of $R^{16}$-$R^{18}$ are deuterium.

Further preferred compounds according to the invention are those wherein, at least two of $R^{19}$-$R^{25}$ are deuterium; at least three of $R^{19}$-$R^{25}$ are deuterium; at least four of $R^{19}$-$R^{25}$ are deuterium; at least five of $R^{19}$-$R^{25}$ are deuterium; at least six of $R^{19}$-$R^{25}$ are deuterium; or at least seven of $R^{19}$-$R^{25}$ are deuterium.

Further preferred compounds according to the invention are those wherein, at least two of $R^{26}$-$R^{30}$ are deuterium; at least three of $R^{26}$-$R^{30}$ are deuterium; at least four of $R^{26}$-$R^{30}$ are deuterium; or five of $R^{26}$-$R^{30}$ are deuterium. In one especially preferred embodiment of the present invention, compounds according to the invention are those wherein five of (i.e. each of) $R^{26}$-$R^{30}$ are deuterium.

Further preferred compounds according to the invention are those wherein at least two of $R^1$-$R^{30}$ are deuterium. Particularly preferred compounds are those wherein at least one of $R^1$-$R^8$ is deuterium and at least one of $R^9$-deuterium; at least one of $R^9$-$R^{15}$ is deuterium and at least one of $R^1$-$R^8$, $R^{16}$-$R^{18}$, $R^{19}$-$R^{25}$ or $R^{26}$-$R^{30}$ is deuterium; at least one of $R^{16}$-$R^{18}$ is deuterium and at least one of $R^1$-$R^8$, $R^9$-$R^{15}$, $R^{19}$-$R^{25}$ or $R^{26}$-$R^{30}$ is deuterium and at least one of $R^1$-$R^8$, $R^9$-$R^{15}$, $R^{16}$-$R^{18}$ or $R^{26}$-$R^{30}$ is deuterium; or at least one of $R^{26}$-$R^{30}$ is deuterium and at least one of $R^1$-$R^8$, $R^9$-$R^{15}$, $R^{16}$-$R^{18}$ or $R^{19}$-$R^{25}$ is deuterium.

In one embodiment of the invention, at least two of $R^1$-$R^8$ are deuterium. For example, compounds according to the invention may be selected from the following group wherein each of the atoms indicated to be deuterium (D) have a deuterium abundance greater than the naturally occurring abundance of deuterium:

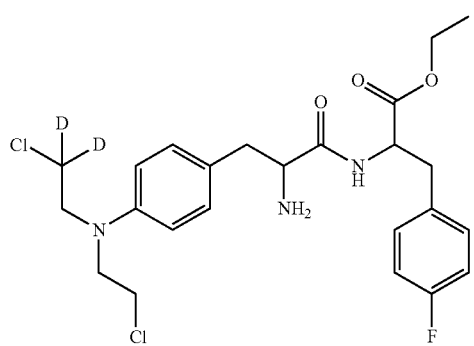

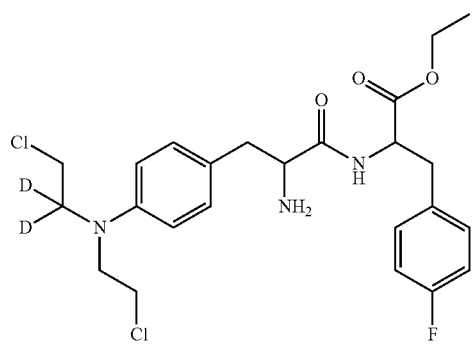

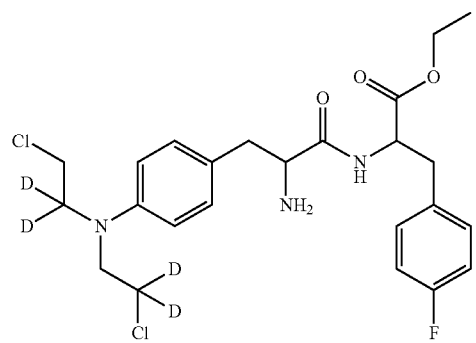

In another embodiment of the invention, at least four of $R^1$-$R^8$ are deuterium. For example, compounds according to the invention may be selected from the following group wherein each of the atoms indicated to be deuterium (D) have a deuterium abundance greater than the naturally occurring abundance of deuterium:

In another embodiment of the invention at least eight of $R^1$-$R^8$ are deuterium. For example, a compound according to the invention has the following structure wherein each of the atoms indicated to be deuterium (D) have a deuterium abundance greater than the naturally occurring abundance of deuterium:

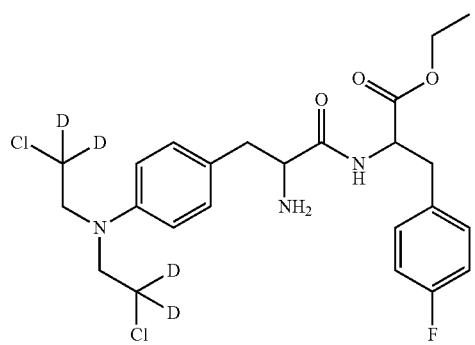

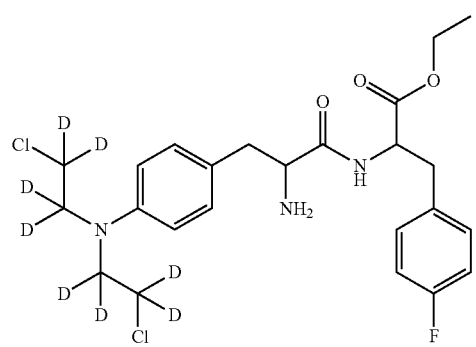 [SMILES: [2H]C([2H])(Cl)C([2H])([2H])N(c1ccc(CC(N)C(=O)NC(Cc2ccc(F)cc2)C(=O)OCC)cc1)C([2H])([2H])C([2H])([2H])Cl]

In another embodiment of the invention, at least two of $R^9$-$R^{15}$ are deuterium, for example least two of $R^9$-$R^{12}$ are deuterium. For example, compounds according to the invention may be selected from the following group wherein each of the atoms indicated to be deuterium (D) have a deuterium abundance greater than the naturally occurring abundance of deuterium:

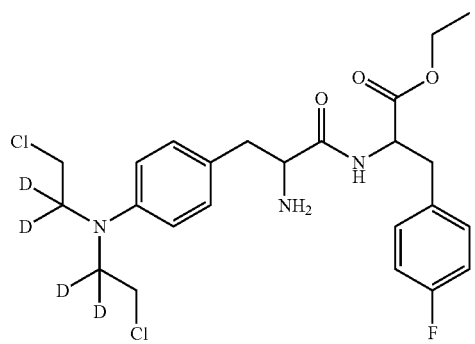

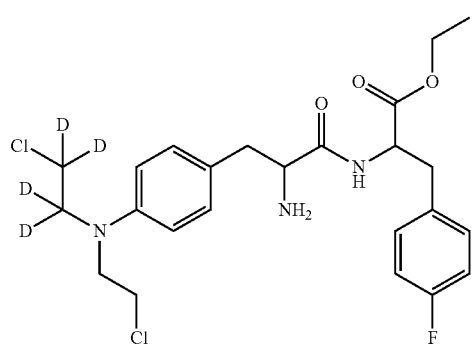

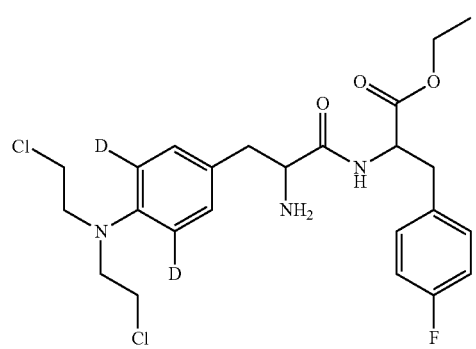

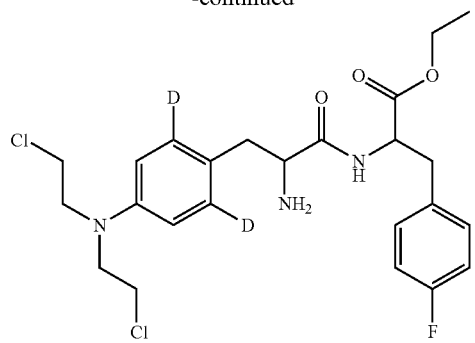

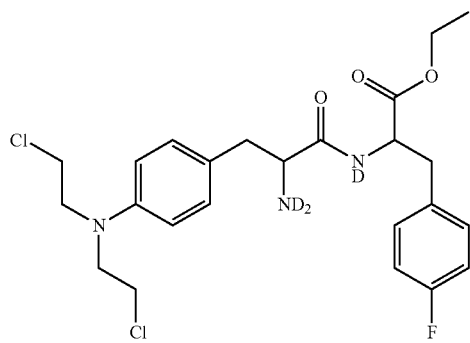

In another embodiment of the invention, at least one of $R^{19}$-$R^{25}$ is a deuterium. For example, a compound according to the invention has the following structure wherein each of the atoms indicated to be deuterium (D) have a deuterium abundance greater than the naturally occurring abundance of deuterium:

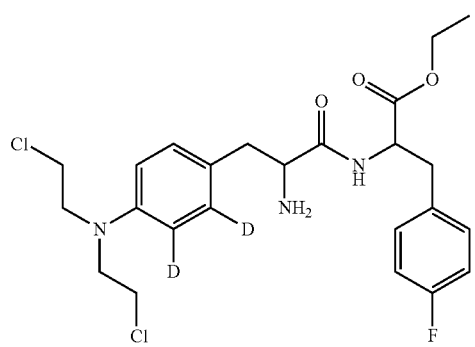

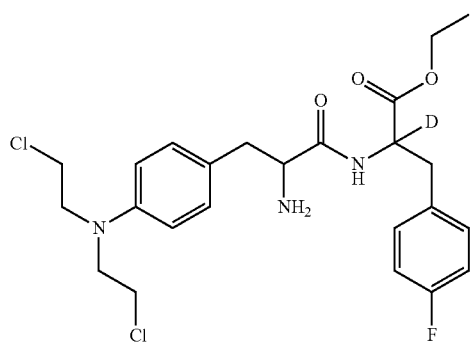 [SMILES: [2H]C(Cc1ccc(F)cc1)(NC(=O)C(N)Cc1ccc(N(CCCl)CCCl)cc1)C(=O)OCC]

In another embodiment of the invention, at least two of $R^{26}$-$R^{30}$ are deuterium. For example, a compound according to the invention has the following structure wherein each of the atoms indicated to be deuterium (D) have a deuterium abundance greater than the naturally occurring abundance of deuterium:

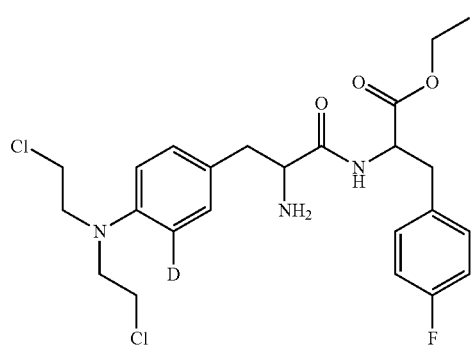

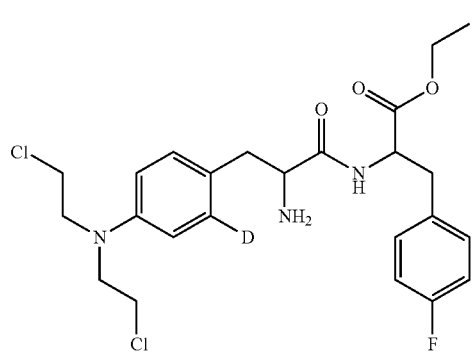

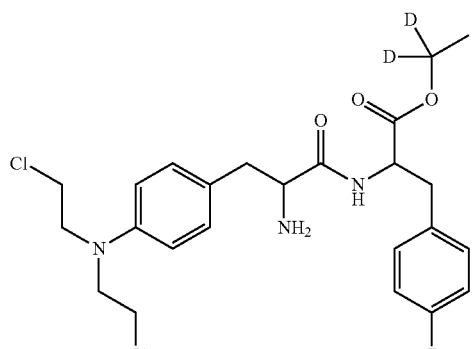

In another embodiment of the invention, at least three of $R^{16}$-$R^{18}$ are deuterium. For example, a compound according to the invention has the following structure wherein each of the atoms indicated to be deuterium (D) have a deuterium abundance greater than the naturally occurring abundance of deuterium:

In another embodiment of the invention, at least three of $R^{26}$-$R^{30}$ are deuterium. For example, a compound according to the invention has the following structure wherein each of the atoms indicated to be deuterium (D) have a deuterium abundance greater than the naturally occurring abundance of deuterium:

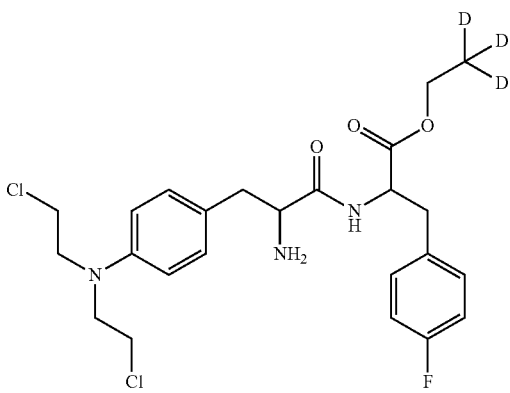 [SMILES: [2H]C([2H])([2H])COC(=O)C(Cc1ccc(F)cc1)NC(=O)C(N)Cc1ccc(N(CCCl)CCCl)cc1]

In an especially preferred embodiment of the invention, five of $R^{26}$-$R^{30}$ are deuterium (i.e. each of $R^{26}$-$R^{30}$ are deuterium). For example, a compound according to the invention has the following structure wherein each of the atoms indicated to be deuterium (D) have a deuterium abundance greater than the naturally occurring abundance of deuterium:

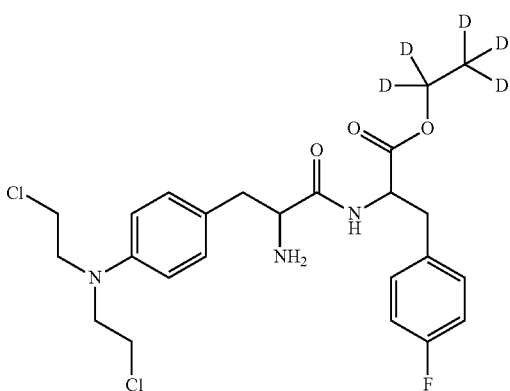 [SMILES: [2H]C([2H])([2H])C([2H])([2H])OC(=O)C(Cc1ccc(F)cc1)NC(=O)C(N)Cc1ccc(N(CCCl)CCCl)cc1]

In another embodiment of the invention, at least one of $R^9$-$R^{15}$ is a deuterium and at least one of $R^{19}$-$R^{25}$ is a deuterium. For example, a compound according to the invention has the following structure wherein each of the atoms indicated to be deuterium (D) have a deuterium abundance greater than the naturally occurring abundance of deuterium:

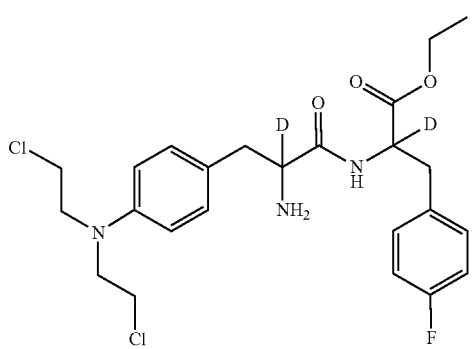 [SMILES: [2H]C(N)(Cc1ccc(N(CCCl)CCCl)cc1)C(=O)NC([2H])(Cc1ccc(F)cc1)C(=O)OCC]

In another embodiment of the invention, at least one of $R^9$-$R^{15}$ is deuterium and at least one of $R^1$-$R^8$ or $R^{26}$-$R^{30}$ is deuterium. For example, compounds according to the invention may be selected from the following group wherein each of the atoms indicated to be deuterium (D) have a deuterium abundance greater than the naturally occurring abundance of deuterium:

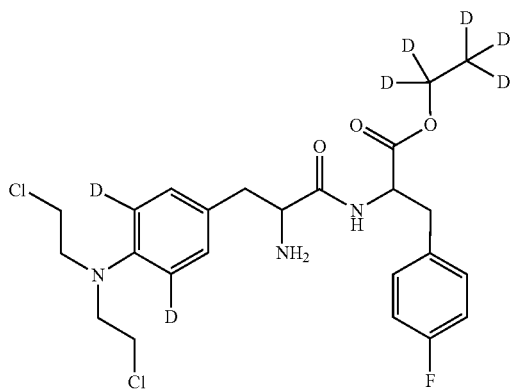

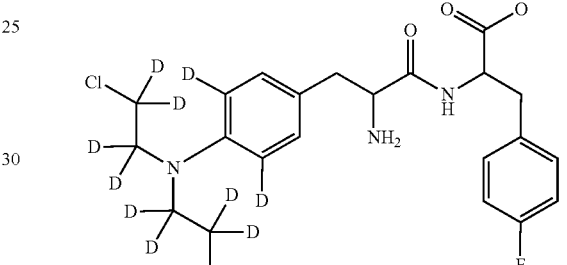

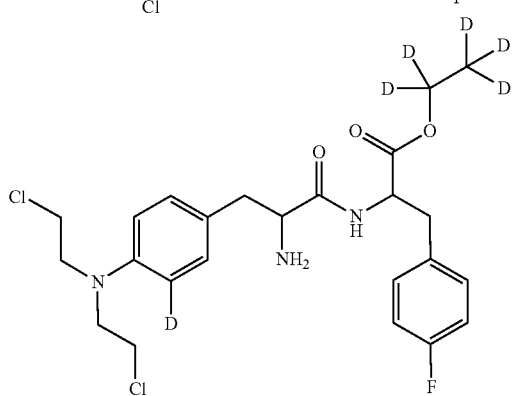

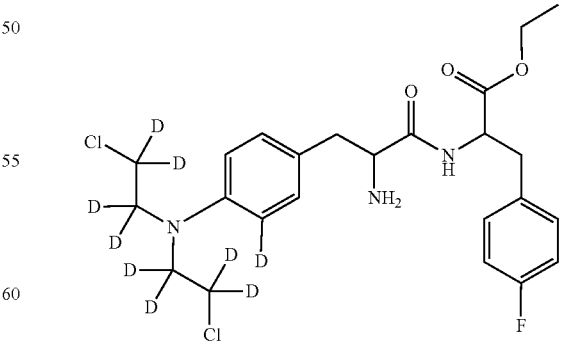

The compounds of the present invention may be prepared using methods known to those skilled in the art of organic chemistry and by routine modification of known procedures for preparing melflufen. Procedures for preparing melflufen are described in WO 01/96367 and WO 2016/180740. Procedures for preparing deuterated compounds are known in the art. See for example Sajiki, New Horizons of Process Chemistry (2017), Springer, pg 29-40, and Hanson, The Organic Chemistry of Isotopic Labelling (2011), Chapter 3, RSC Publishing.

The compounds of the present invention may be prepared by synthetic techniques that employ deuterated reagents. Alternatively, deuterium may be introduced by the reduction of reducible moieties using deuterated reducing agents. A further alternative approach is use of post-synthetic hydrogen-deuterium exchange reactions using $D_2$ gas in the presence of a metal catalyst, for example a Pd/C or Pt/C catalyst.

The compounds of the present invention may be prepared by using a combination of deuterated and non-deuterated reagents. Suitable deuterated reagents are those wherein each deuterium has an abundance level greater than the naturally occurring abundance of deuterium. For example an abundance level of at least 1 mol %, 5 mol %, 10 mol %, 50 mol %, 90 mol % or 98 mol % deuterium. Suitable deuterated reagents include deuterated chloroacetic acid, deuterated chloroethanol, deuterated ethylene oxide, deuterated ethanol, deuterated para-fluoro-phenylalanine, deuterated para-nitro-phenylalanine and deuterated para-amino-phenylalanine. Deuterated reagents can be purchased from commercial suppliers. Alternatively, they may be prepared from non-deuterated reagents using a hydrogen-deuterium exchange reaction as described above.

The compounds of the present invention may also be prepared by using deuterated reducing agents. Suitable deuterated reducing agents include deuterated borane, deuterated borane-Lewis base complex, borodeuteride, a metal deuteride, and $D_2$ gas in the presence of a metal catalyst.

The compounds of the present invention may be also prepared from melflufen using a hydrogen-deuterium exchange reaction.

Specific methods for preparing compounds according to the invention are described herein in the Examples section.

For the avoidance of doubt, in this document, when the term "deuterated melflufen" is used, it includes salt(s) thereof, unless stated otherwise. Melflufen, and salts thereof, especially the hydrochloride salt thereof, are known from, for example, WO 01/96367 and WO 2014/065751, and the same salts are suitable for use in the present invention.

Salts of deuterated melflufen which are suitable for use in the present invention are those wherein a counterion is pharmaceutically acceptable. Suitable salts include those formed with organic or inorganic acids. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)-alkyl- or aryl-sulfonic acids which are unsubstituted or substituted, for example by halogen. Pharmaceutically acceptable acid addition salts include those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxalic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine and arginine.

Preferred salts of deuterated melflufen include acid addition salts such as those formed from hydrochloric, hydrobromic, acetic, p-toluenesulfonic, tartaric, sulphuric, succinic, phosphoric, oxalic, nitric, methanesulfonic, malic, maleic and citric acid. More preferably, the salt of deuterated melflufen according to the present invention is the hydrochloride salt (i.e. the addition salt formed from hydrochloric acid).

Those skilled in the art of organic chemistry will appreciate that many organic compounds can form complexes with solvents in which they are reacted or from which they are precipitated or crystallized. These complexes are known as "solvates". For example, a complex with water is known as a "hydrate". The complex may incorporate a solvent in stoichiometric or non-stoichiometric amounts. Solvates are described in Water-Insoluble Drug Formulation, $2^{nd}$ ed R. Lui CRC Press, page 553 and Byrn et al Pharm Res 12(7), 1995, 945-954. Before it is made up in solution, the deuterated melflufen of formula (I) and (Ia), or salt thereof, for use in the present invention may be in the form of a solvate. Solvates of deuterated melflufen that are suitable for use as a medicament are those wherein the associated solvent is pharmaceutically acceptable. For example a hydrate is pharmaceutically acceptable solvate.

While it is possible for a compound according to the invention to be administered alone, it is preferable for it to be present in a composition and particularly in a pharmaceutical composition. Pharmaceutical compositions include those suitable for oral, parenteral (including subcutaneous, intradermal, intraosseous infusion, intramuscular, intravascular (bolus or infusion), and intramedullary), intraperitoneal, transmucosal, transdermal, rectal and topical (including dermal, buccal, sublingual and intraocular) administration although the most suitable route may depend upon for example the condition and disorder of the subject under treatment.

Pharmaceutical compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The deuterated melflufen may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2S, 1988.

Pharmaceutical compositions for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. Preferably the formulations may be presented in unit dosage or divided dosage containers, for example sealed ampoules and vials. The formulation may be stored in a freeze-dried (lyophilised) condition requiring only the addition of the sterile liquid carrier, for example saline or water-for-injection, immediately prior to use. Such lyophilised formulations are known from WO2012/146625 and WO2014/065751 for the established melflufen compound. The compounds of the current invention can be formulated in a similar way, for example in a lyophilised form containing the active ingredient and sucrose, for example in a weight ratio of from 1:25 to 1:75, for example 1:50. Extemporaneous injection and infusion solutions and suspensions may be prepared from sterile powders, granules or other dry composition. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Pharmaceutical compositions for nasal, aerosol or inhalation administration include solutions in saline, which can contain, for example, benzyl alcohol or other suitable preservatives, absorption promoters to enhance bioavailability, and/or other solubilizing or dispersing agents such as those known in the art.

Pharmaceutical compositions for rectal administration may be presented as a suppository with the usual carriers such as cocoa butter, synthetic glyceride esters or polyethylene glycol. Such carriers are typically solid at ordinary temperatures, but liquefy and/or dissolve in the rectal cavity to release the drug.

Pharmaceutical compositions for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Compounds, compositions and pharmaceutical compositions according to the invention may be used in the treatment and/or prophylaxis of cancer, reducing tumour growth and/or killing tumour cells. Thus, deuterated melflufen may be used for curing and/or prolonging the survival of patients afflicted with cancer diseases. The present invention is especially useful in the treatment and/or prophylaxis of multiple myeloma, breast cancer, lung cancer, ovarian cancer, leukaemias and lymphomas, in particular when the condition has relapsed or is refractory. The present invention finds particular use in the treatment of relapsed refractory multiple myeloma.

The amount of deuterated melflufen which is required to achieve a therapeutic effect will vary with particular route of administration and the characteristics of the subject under treatment, for example the species, age, weight, sex, medical conditions, the particular disease and its severity, and other relevant medical and physical factors. An ordinarily skilled physician can readily determine and administer the effective amount of deuterated melflufen required for treatment or prophylaxis of cancer.

Deuterated melflufen, or salt thereof, may be administered daily, every second or third day, weekly, every second, third or fourth week or even as a high single dose depending on the subject and cancer form to be treated.

Preferably, deuterated melflufen, or salt thereof (excluding the mass of any salt), may be administered in an amount of about 15 to 150 mg per administration. For example, 15, 20, 25, 40, 50, 60, 70, 80, 90, 100, 110, 120, 130, 140 or 150 mg.

Alternatively, the deuterated melflufen, or salt thereof (excluding the mass of any salt), may be administered in a single high dose. A single high dose may be about 150 to 1200 mg, for example about 150 to 800 mg. For example, it may be selected from 150, 200, 300, 400, 500, 600, 700, 800, 900, 1000, 1100 and 1200 mg. For example, it may be selected from 150, 200, 300, 400, 500, 600, 700 and 800 mg.

Whilst deuterated melflufen, or salt thereof, may be used as the sole active ingredient in the present invention, it is also possible for it to be used in combination with one or more further therapeutic agent(s), and the use of such combinations provides one preferred embodiment of the invention. Such further therapeutic agents may be agents useful in the treatment or prophylaxis of cancer, or other pharmaceutically active materials. Such agents are known in the art. Examples of further therapeutic agents for use in the present invention include steroids (prednisone and dexamethasone), IMiDs (thalidomide, lenalidomide and pomalidomide), PIs (bortezomib and carfilzomib), histone deacetylase (HDAC) inhibitors (panobinostat) and conventional chemotherapy (alkylators (e.g. melphalan, cyclophosphamide) and doxorubicin).

EXAMPLES

Synthesis of Compound of the Invention
General Experimental Details
Unless stated otherwise, all reagents and solvents were purchased from commercial sources and used without further purification. Melflufen and melflufen intermediates can be prepared using the synthesis methods described in WO 2016/180740 or in WO 01/96367.

Analytical HPLC/LCMS was performed using an Agilent 1100 series Liquid Chromatography/Mass Selective Detector (MSD, Single Quadrupole) equipped with an electrospray interface and a UV diode array detector. Analyses were performed by two methods using either an ACE 3 C8 (3.0×50 mm) column with a 10-97% gradient of acetonitrile in 0.1% aqueous TFA over 3 min and a flow of 1 mL/min (condition #1), or an Xbridge C18 (3.0×50 mm) column with a 10-97% gradient of acetonitrile in 10 mM ammonium bicarbonate over 3 min and a flow of 1 mL/min (condition #2), both with UV detection at 305 nm. 1H NMR spectra were recorded on a Bruker 400 MHz instrument at 25° C. Preparative HPLC was performed on a Gilson system equipped with a UV detector using an Xbridge Prep C18 5 µM OBD (19×50 mm) column, with acetonitrile and 50 mM ammonium bicarbonate as buffer.

Example 1

Synthesis of (2S)-2-[[(2S)-2-amino-3-[4-[bis(2-chloroethyl)amino]phenyl]propanoyl]amino]-3-(4-fluorophenyl)propanoic acid (II)

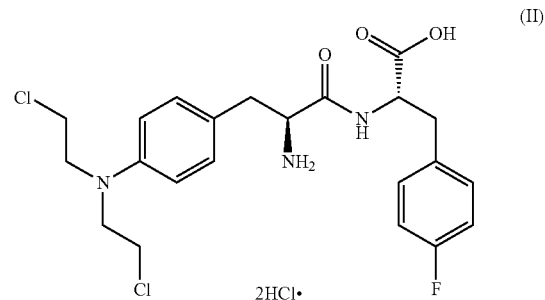 [SMILES: N[C@@H](Cc1ccc(N(CCCl)CCCl)cc1)C(=O)N[C@@H](Cc1ccc(F)cc1)C(=O)O]

Melflufen hydrochloride (500 mg, 0.93 mmol) was suspended in water (10 mL) followed by addition of concentrated HCl (10 mL). The reaction mixture was stirred at room temperature for 24 hours. Toluene was added to the reaction mixture and the solution concentrated in vacuo. This process was repeated three times. The solution was then evaporated to dryness in vacuo. The crude mixture was used as the starting material for Example 2.

Example 2

Synthesis of melflufen-d5 (III), melflufen-d6 (IV) and melflufen-d7 (V)

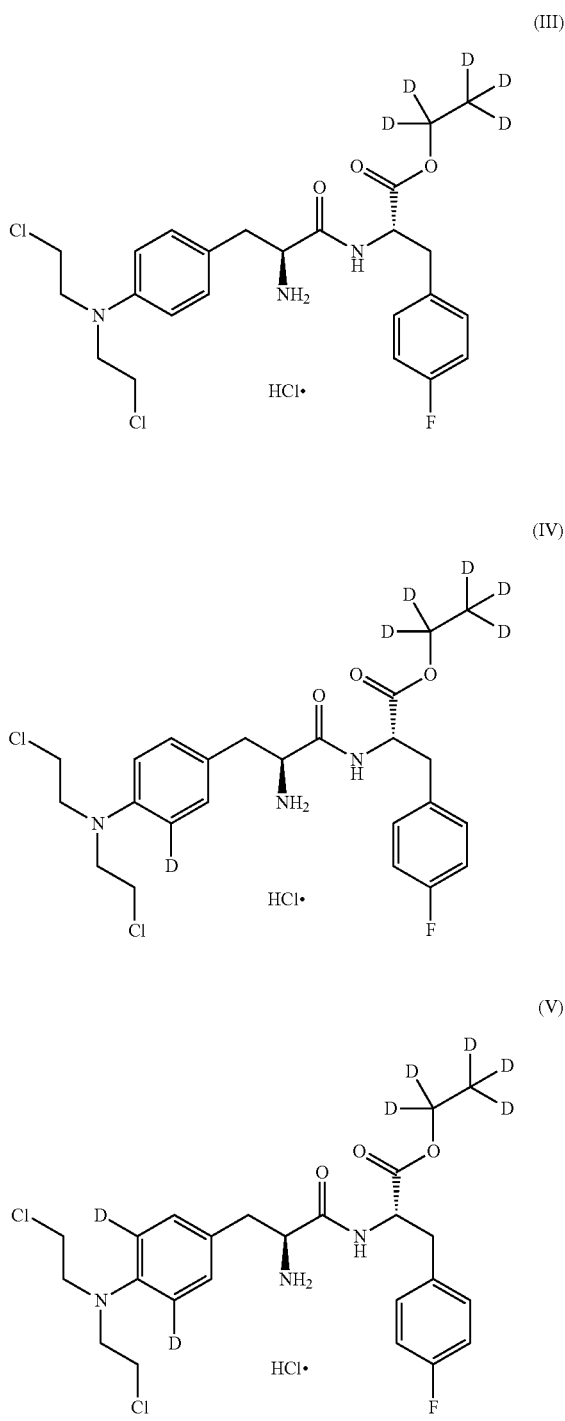

Compound II (507 mg, 0.93 mmol) was dissolved in ethanol-d6 (4.86 g, 93.32 mmol) and refluxed. After 2 hours there was near complete conversion of compound II to the ester. The reaction mixture was cooled to room temperature and then evaporated to dryness in vacuo to afford a white solid (495 mg, 95%).

NMR of the final compound showed partial deuteration at the ortho positions of the aniline function. Integration of the doublet at δ 6.78-6.82 ppm suggested that the final sample was a heterogeneous mixture of melflufen-d5 (III), melflufen-d6 (IV) and melflufen-d7 (V), with the final sample comprising approximately 12.5% melflufen-d5 (III). Deuterium-proton exchange is known to occur with protons in an aniline function under heat and acidic conditions in a deuterated solvent. LC-MS (condition #1): tR 2.28 min (purity>97%), m/z [M+H] 505. LC-MS (condition #2): tR 2.63 min (purity>98%), m/z [M+H] 505. 1H NMR (400 MHz, MeOD): δ/ppm; 2.92-2.97 (m, 1H), 3.01-306 (m, 1H), 3.16-3.21 (dd, 2H), 3.67-3.71 (m, 4H), 3.78-3.81 (m, 4H), 4.02-4.05 (m, 1H), 4.69-4.73 (m, 1H), 6.78-6.82 (d, 0.25H), 7.02-7.07 (t, 2H), 7.19 (s, 2H), 7.24-7.28 (m, 2H).

Example 3

Synthesis of ethyl (2S)-2-[[(2S)-3-[4-[bis(1,1,2,2-tetradeuterio-2-hydroxy-ethyl)amino]phenyl]-2-(tert-butoxycarbonylamino)propanoyl]amino]-3-(4-fluorophenyl)propanoate (VI)

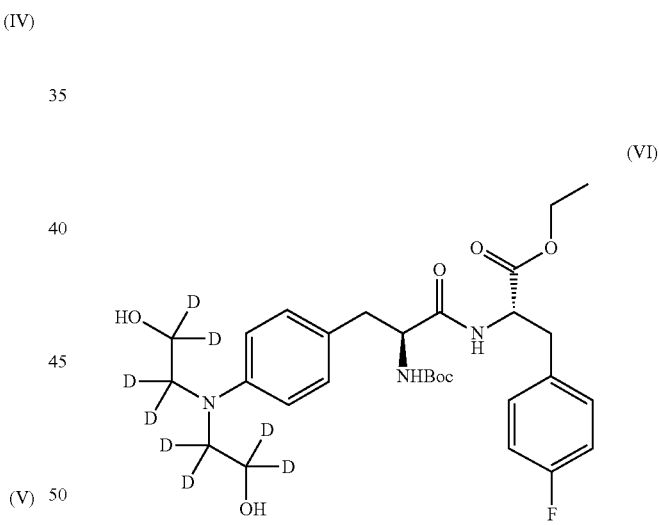

Ethyl (2S)-2-[[(2S)-3-(4-aminophenyl)-2-tertbutoxycarbonylamino)propanoyl]amino]-3-(4-fluorophenyl)propanoate (470 mg, 0.99 mmol, see WO 2016/180740 for a suitable synthesis method) was suspended in acetonitrile. Na2CO3 (210.42 mg, 1.99 mmol) was added to the reaction mixture at room temperature. The reaction mixture was then stirred for 15 minutes before adding 1,1,2,2-tetradeuterio-2-iodo-ethanol (0.17 mL, 2.18 mmol). The reaction mixture was stirred for a month at reflux. After cooling, the reaction was divided over DCM and water, and extracted with DCM. The organic phase was concentrated and the product purified by preparative HPLC to afford the title compound (0.29 g, 51%).

Example 4

Synthesis of melflufen-d8 (VII)

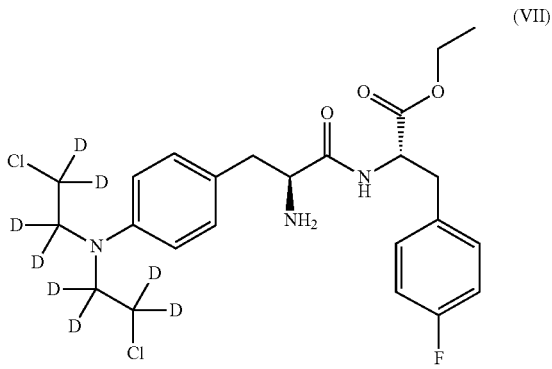 [SMILES: [2H]C([2H])(Cl)C([2H])([2H])N(c1ccc(C[C@H](N)C(=O)N[C@@H](Cc2ccc(F)cc2)C(=O)OCC)cc1)C([2H])([2H])C([2H])([2H])Cl]

(VII)

Compound VI (290 mg, 0.51 mmol) was dissolved in DCM followed by slow addition of POCl$_3$. The reaction mixture was stirred at room temperature overnight. The reaction mixture was divided over water and DCM, and then basified by adding 1 M NaOH. The title compound was extracted with diethyl ether and the solvent evaporated in vacuo to afford the title compound as a pale yellow foam of approximately 95% purity (96 mg, 37%). LC-MS (condition #1): $t_R$ 2.27 min, m/z [M+H] 506. LC-MS (condition #2): tR 2.63 min, m/z [M+H] 506. 1H NMR (400 MHz, MeOD): δ/ppm; 1.00-1.15 (t, 3H), 2.80-2.84 (m, 1H), 2.91-2.95 (m, 1H), 3.04-3.09 (dd, 2H), 3.90-3.94 (m, 1H), 4.03-4.08 (q, 2H), 4.58-4.62 (m, 1H), 6.68-6.70 (d, 2H), 6.90-6.94 (t, 2H), 7.07-7.10 (d, 2H), 7.13-7.17 (m, 2H).

Example 5

Preparation of (2S)-2-[[(2S)-2-amino-3-[4-[bis(2-chloro-1,1,2,2-tetradeuterioethyl)amino]phenyl]propanoyl]amino]-3-(4-fluorophenyl)propanoate (VIII)

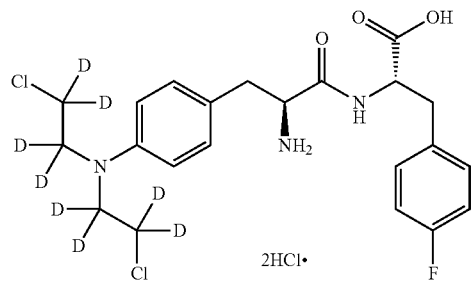

(VIII)

Compound VII (20 mg, 0.04 mmol) was suspended in water (3 mL) followed by addition of concentrated HCl (3 mL). The reaction mixture was stirred overnight at room temperature. Toluene was added to the reaction mixture and the solution concentrated in vacuo. This process was repeated three times. The residue was dissolved in acetonitrile/water and transferred to a vial followed by removal of the solvent using a N2 stream to give the title compound (13.7 mg, 64%). LC-MS (condition #1): $t_R$ 1.97 min (purity>95%), m/z [M+H] 478. LC-MS (condition #2): $t_R$ 1.72 min (purity>94%), m/z [M+H] 478.

Example 6

Biological Activity

The fluorometric microculture cytotoxicity assay (FMCA) (Larsson, R., et al-1992: Int J Cancer, 50,177-185) is used to evaluate the compounds. Briefly, 96-well microtiter plates (NUNC, Roskilde, Denmark) are prepared with 20 µl drug solution at ten times the desired concentration and stored for up to two months at −70° C. In general the substances are first dissolved in absolute or acidic ethanol to concentrations of 4.0 to 8.2 mM and further diluted with sterile water or sterile phosphate buffered saline. All dilutions with water are made directly before the experiments to minimise the influence of mustard hydrolysis. Final ethanol concentrations do not exceed 1% v/v. At day zero of the experiment 180 µL of cell suspension of adequate concentration is added to the wells of the thawed plate, six wells serve as controls (cell suspension only) and six wells as blanks (cell medium only). After 72 hours incubation the cells are washed once with PBS, and 100 µL of fluorescein diacetate (10 µg/ml) in a physiological buffer is added. After another 45 min the generated fluorescence (ex 485 rim; em 528 nm) is measured in a 96-well scanning fluorometer (Fluoroscan II, Labsystems Oy, Helsinki, Finland). The generated fluorescence is proportional to the number of living cells, and data are presented as survival index (fluorescence in test well in percent of control wells with blank values subtracted) and IC$_{50}$ (inhibitory concentration 50%, as calculated by the software GraphPad Prism@ (Graphpad Software Inc., San Diego, CA, USA). Quality criteria for a successful assay include a coefficient of variation less than 30% in blank (six wells), control (six wells) and test wells (three) respectively, a control signal more than ten times the blank and finally an initial cell viability of more than 70% (primary human tumour cultures) or 90% (cell lines) as judged by the trypan blue exclusion test.

Fluorescein diacetate (FDA, Sigma) is dissolved in DMSO to 10 mg/ml and kept frozen as a stock solution in the dark. Cell growth medium RPMI-1640 (Sigma) supplemented with 10% heat-inactivated fetal calf serum (FCS, Sigma chemical Co., St. Louis, MO), 2 mM glutamine, 100 µg/ml streptomycin, and 100 µg/ml penicillin, is used.

Example 7a

Production of ($^2$H$_5$)ethyl(2S)-2-amino-3-(4-fluorophenyl)propanoate hydrochloride by esterification of p-fluoro-L-phenylalanine with Ethanol (d6)

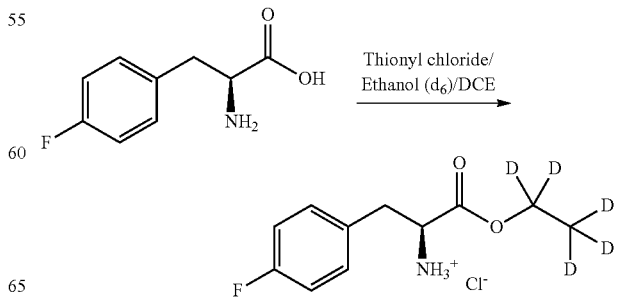

p-Fluoro-L-phenylalanine (1.0 kg, CAS Number 1132-68-9) was slurried in a mixture of ethanol-d6 (2.5 l, CAS Number: 1516-08-1) and 1,2-dichloroethane (2.0 l). A scrubber containing NaOH (5M solution) was connected to the outlet of the reactor, after the condenser. In order to follow the degradation of the scrubber fluid, bromothymol blue (1-2 mg) was added.

The reactor was heated to an inner temperature of 60° C. When the inner temperature reached 60° C., addition of thionyl chloride (600 ml) at a slow rate was started. Initially a very thick precipitate was formed. The initially very thick slurry thinned during the course of the reaction. Total time for the addition was ca. 3 h. The inner temperature was allowed to reach a maximum of 70° C. and was controlled by adjusting the mantel temperature accordingly. After full addition the mantel temperature was adjusted to keep the inner temperature between 65-70° C.

Full conversion to the desired ($^2H_5$)ethyl(2S)-2-amino-3-(4-fluorophenyl)propanoate hydrochloride was achieved after 3 h after point of complete addition of the thionyl chloride. After full conversion was confirmed (LC-MS analysis with conditions as follows: ACE 3 C8 (3.0×50 mm) column, with a 10-90% B gradient over 3 min; Mobile phase A, water 0.1% TFA, mobile phase B, pure acetonitrile, flow of 1 mL/min, UV detection at 215-395, 254 and 220 nm), the reaction was cooled (inner temperature ca. 45° C.) and tert-butyl methyl ether (12.5 litres) was added giving the product as a white precipitate. The mixture was stirred in order to get a homogeneous mixture.

The mixture was then cooled to an inner temperature of 0° C. and matured at this temperature for ca. 30 min before filtration. The solid ($^2H_5$)ethyl(2S)-2-amino-3-(4-fluorophenyl)propanoate hydrochloride was washed with ca. 1 litre of tert-butyl methyl ether and then dried at a maximum temperature of 30° C. under reduced pressure. The product was sieved carefully in order to remove lumps, if present. Isolated yield of ($^2H_5$)ethyl(2S)-2-amino-3-(4-fluorophenyl) propanoate hydrochloride was 92%. LC-MS: tR 1.43 min, m/z [M+H] 217.

Example 7b

Kg Scale Production of ($^2H_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate (IX)

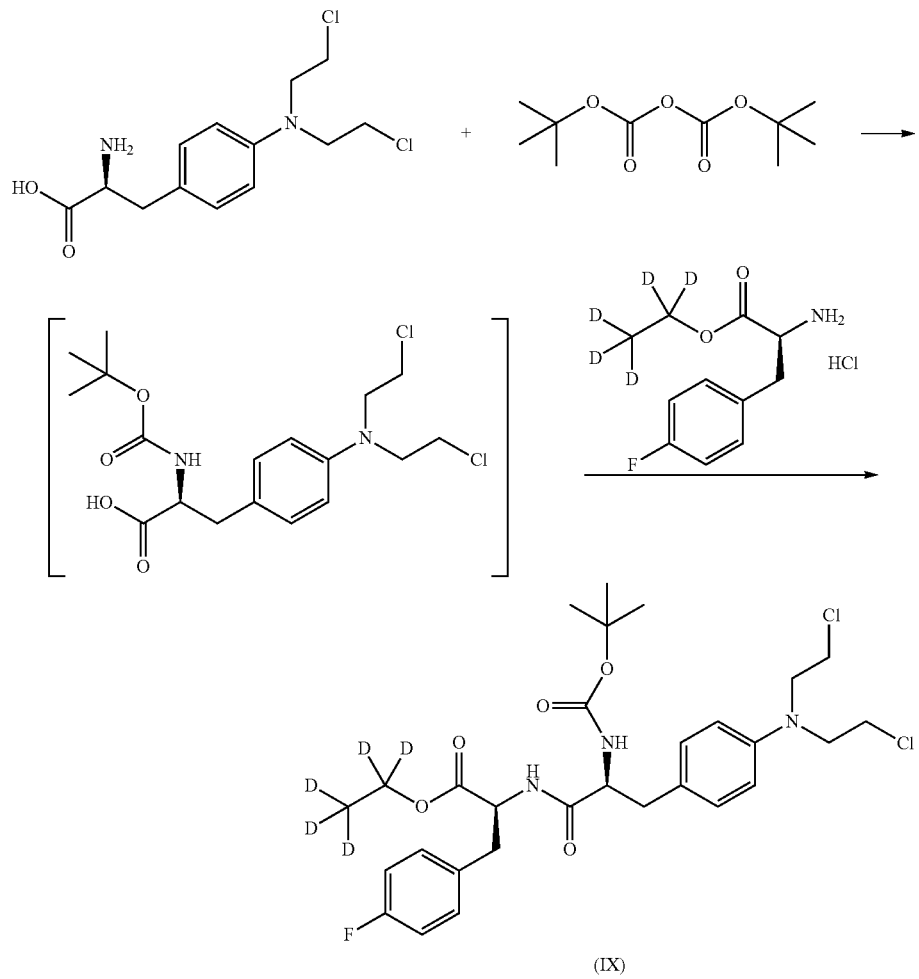

(IX)

Melphalan (1.663 kg, 5.45 mol, 1 eq.) was added to a mixture of purified water (16.0 kg), NaOH (32%, aq., 1.04 kg) and tetrahydrofuran (10.0 kg) at 10-15° C. A mixture of di-tert-butyl dicarbonate (1.308 kg, 5.99 mol, 1.1 eq.) and tetrahydrofuran (4.75 kg) was added at 10-15° C. The reaction mixture was stirred for 4-5 h at 18-23° C. until minimum 97.0% (HPLC) conversion of Melphalan into was achieved. The temperature was adjusted to 15-20° C., and while keeping this temperature, pH was adjusted to 2.5-3.0 with 1.5 M HCl. Ethyl acetate (7.34 kg) was added, and the phases were separated. The aqueous phase was extracted with ethyl acetate (7.34 kg). The combined organic phases were dried with magnesium sulfate, filtered, and the filter cake was washed with ethyl acetate. The solvents were removed by distillation in vacuo and the residue containing (2S)-3-{4-[bis(2-chloroethyl)amino]phenyl}-2-{[(tert-butoxy)carbonyl]-amino}propanoic acid was dried in vacuo for minimum 12 h at 20-25° C. HPLC: retention time 11.9 min. (HPLC conditions were as follows: sample solvent acetonitrile:water, 1:1 (v/v), Waters, Atlantic T3 (3 µ, 4.6× 150 mm) column, 10-90-10% B gradient over 23 min, flow of 1 mL/min, mobile phase A: 500 µL phosphoric acid 85% in 1.0 L MQ-water, mobile phase B: 500 µL phosphoric acid 85% in 1.0 acetonitrile, with UV detection at 262 nm).

The (2S)-3-{4-[bis(2-chloroethyl)amino]phenyl}-2-{[(tert-butoxy)carbonyl]-amino}propanoic acid residue was redissolved in dichloromethane (44.0 kg). 4-Methylmorpholine (1.378 kg, 13.63 mol, 2.5 eq.) was added, followed by ($^2$H$_5$)ethyl(2S)-2-amino-3-(4-fluorophenyl)propanoate hydrochloride (1.377 kg, 5.45 mol, 1.0 eq.), 1-hydroxybenzotriazole, H$_2$O (0.083 kg, 0.54 mol, 0.1 eq.) and N-(3-dimethylaminopropyl)-N'-ethylcarbodiimide, HCl (1.045 kg, 5.45 mol, 1.0 eq.). The reaction mixture was stirred for 3-4 h at 18-23° C., until minimum 97.0% (HPLC) conversion of (2S)-3-{4-[bis(2-chloroethyl)amino]phenyl}-2-{[(tert-butoxy)carbonyl]-amino}propanoic acid into ($^2$H$_5$) ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate was achieved (HPLC conditions were as follows: sample solvent acetonitrile, Waters, Atlantic T3 (3µ, 4.6×150 mm) column, 10-90-10% B gradient over 23 min, flow of 1 mL/min, mobile phase A: 500 µL phosphoric acid 85% in 1.0 L MQ-water, mobile phase B: 500 µL phosphoric acid 85% in 1.0 acetonitrile, with UV detection at 262 nm.).

pH was adjusted to 3.0-4.0 with 5% KHSO4 (aq.). The organic phase was secured and the aqueous phase was extracted with dichloromethane (29.0 kg). The first organic phase was washed with 6% NaHCO$_3$. The organic phase was secured and the remaining aqueous phase was back-extracted with the second organic phase. The combined organic phases were dried with magnesium sulfate, filtered, and washed with dichloromethane. The dried organic phase was concentrated by distillation in vacuo to 22-26 L. The reduced organic phase was applied to column chromatography (silica gel (40-63 pm, 22.4 kg), n-heptane (6.7 kg) and dichloromethane (52.2 kg)). The column was eluted with 6% ethyl acetate/dichloromethane. The fractions containing ($^2$H$_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate (TLC) were combined and evaporated under reduced pressure to 26-28 L. Ethyl acetate (5.8 kg) was added, and the evaporation was continued to 26-28 L. This procedure was repeated. After addition of ethyl acetate precipitation of ($^2$H$_5$)ethyl (2S)-24(2S)-3-{4-[bis(2-chloroethyl)amino]phenyl}-2-{[(tert-butoxy)carbonyl]-amino}propanamido]-3-(4-fluorophenyl)propanoate started. Optionally, seed crystals of ($^2$H$_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate may be added to assist the precipitation. Ethyl acetate (5.8 kg) was added again, and the optional seeding step may be repeated. The mixture was evaporated under reduced pressure to 19-21 L and n-heptane (22.1 kg) was added at 35-45° C. The suspension was cooled to −2 to 2° C. and stirred for 2-18 h. The solid was isolated by centrifugation, and the filter cake was washed with n-heptane. The solid was dried in vacuo at 30° C. to give ($^2$H5)ethyl (2S)-2-[(2S)-3-{4-[bis (2-chloroethyl)amino]phenyl}-2-{[(tert-butoxy)carbonyl]-amino}propanamido]-3-(4-fluorophenyl)propanoate (2.6 kg, 80%) as a white to slightly yellow solid material. HPLC: retention time 13.4 min.

Example 7 c: Kg scale production of melflufen-d5 (III) (($^2$H$_5$) ethyl (2S)-2-[(2S)-2-amino-3-{4-[bis(2-chloroethyl) amino]phenyl}propanamido]-3-(4-fluorophenyl) propanoate hydrochloride)

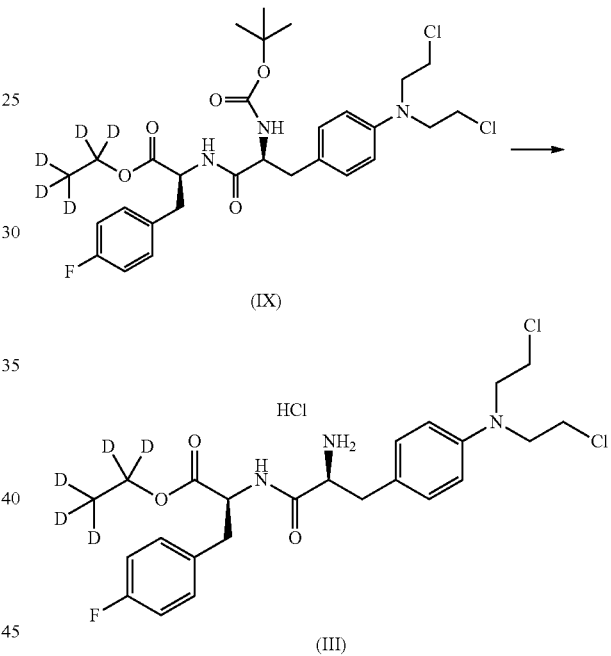

A solution of ($^2$H$_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate (compound IX) (3.10 kg, 5.14 mol) in 1.3 M HCl in acetonitrile prepared from hydrogen chloride (1.31 kg 35.9 mol) and acetonitrile (21.7 kg) was stirred for 12-24 hours at 29-33° C. A conversion of ($^2$H$_5$)ethyl (2S)-2-[(2S)-3-{4-[bis(2-chloroethyl)amino]phenyl}-2-{[(tert-butoxy)carbonyl]-amino}propanamido]-3-(4-fluorophenyl)propanoate into ($^2$H$_5$)ethyl (2S)-2-[(2S)-2-amino-3-{4-[bis(2-chloroethyl) amino]phenyl}propanamido]-3-(4-fluorophenyl)propanoate hydrochloride of minimum 99.0% (HPLC) was obtained (HPLC conditions were as follows: sample solvent DMSO acetonitrile, 1:9 (v/v), Waters, Atlantic T3 (3µ, 4.6×150 mm) column, 10-90-10% B gradient over 23 min, flow of 1 mL/min, mobile phase A: 500 µL phosphoric acid 85% in 1.0 L MQ-water, mobile phase B: 500 µL phosphoric acid 85% in 1.0 acetonitrile, with UV detection at 262 nm.).

The reaction mixture was subjected to polish filtration and diluted with acetonitrile (68.9 kg). Distillation at reduced pressure was then performed using a jacket temperature of 45° C. When the volume of the reaction mixture was 86 L, acetonitrile (22.7 kg) was added and the distillation continued. When 86 L of reaction mixture was left, acetonitrile (22.7 kg) was added and the distillation continued. When the volume in the reactor was 86 L, acetonitrile (22.7 kg) was added and distillation continued until a volume of 86 L in the reactor was reached.

tert-Butyl methyl ether (68.4 kg) was added over a period of 25-45 min at 35-45° C. followed by cooling to 22-28° C. After stirring at this temperature for 60-120 min, crude ($^2H_5$)ethyl (2S)-2-[(2S)-2-amino-3-{4-[bis(2-chloroethyl)amino]phenyl}propanamido]-3-(4-fluorophenyl)propanoate hydrochloride was filtered off and washed with tert-butyl methyl ether (12.5 kg). The crude material was dried in vacuum in the reactor using a jacket temperature set point of 30° C.

Acetonitrile (84.0 kg) was added and the resulting suspension is stirred for 30-90 min at 48-54° C. followed by cooling to 40-45° C. tert-Butyl methyl ether (74.6 kg) was added over a period of 40-70 min at 38-45° C. followed by cooling to 22-28° C. After stirring at this temperature for 60-120 min, crude ($^2H_5$)ethyl (2S)-2-[(2S)-2-amino-3-{4-[bis(2-chloroethyl)amino]phenyl}propanamido]-3-(4-fluorophenyl)propanoate hydrochloride was filtered off and washed with tert-butyl methyl ether (14.0 kg). Drying in vacuum at 30-35° C. provided ($^2H_5$)ethyl (2S)-2-[(2S)-2-amino-3-{4-[bis(2-chloroethyl)amino]phenyl}propanamido]-3-(4-fluorophenyl)propanoate hydrochloride (melflufen-d5, (III)) (2.5 kg, 90%) as a white to off-white solid.

HPLC: retention time 9.0 min.

Biological Testing

Example (a)

In Vivo Study in Dogs

A comparative single dose toxicity study in dogs was carried out, comparing melflufen-d5 (III) and melflufen to investigate the toxicokinetics of melflufen and melflufen-d5 (III) and their metabolites, desethyl-melflufen and melphalan, after a single intravenous administration of melflufen-d5 (III) or melflufen as 30 minutes infusion in the dog.

(i) Introduction and Objectives

This study aimed to compare the potential acute toxicity of melflufen-d5 (III) and melflufen. The toxicokinetics of melflufen-d5 (III), melflufen and their metabolites desethyl-melflufen and melphalan were evaluated after a single intravenous administration as 30 minutes infusion in dogs.

(ii) Materials and Methods

Abbreviations

The following abbreviations are used in this document:

$AUC_\infty$ Area under plasma concentration vs. time curve up to infinite time
$AUC_{last}$ Area under plasma concentration vs. time curve up to the last detectable concentration
$C_{last}$ Last detectable plasma concentration
$C_{max}$ Maximum plasma concentration
% CV Coefficient of variation of the mean as percent
h Hour
SD standard deviation
$t_{1/2,z}$ Apparent terminal half-life
$T_{last}$ Time of the last detectable concentration
$T_{max}$ Time of the maximum concentration
% AUC extr Percent of extrapolated area Study Design Melflufen-d5 (III) or melflufen were given as 30 minutes infusion to male and female dogs according to the following scheme:

| Test Group | Administered compound | Dose (mg/kg) | Volume (mL/kg) | Conc (mg/mL) | Number of Animals Males | Females |
|---|---|---|---|---|---|---|
| 1 | 5% glucose solution | 0 (vehicle) | 5 | 0 | 3 | 3 |
| 2 | melflufen-d5 (III) | 1.25 | 5 | 0.25 | 3 | 3 |
| 3 | melflufen-d5 (III) | 2.5 | 5 | 0.5 | 3 | 3 |
| 4 | melflufen | 2.5 | 5 | 0.5 | 3 | 3 |

The control group was treated with 5% glucose solution.

Sample Collection

Blood samples were collected from peripheral vein on Day 1 at pre-dose, 15 min, 30 min (just prior to end of infusion), 40 min, 1 h, 2 h, 4 h and 6 h after the start of infusion).

Blood samples were collected into heparinized collection tubes, put in an ice-water bath and immediately centrifuged (3 minutes, 10000 g, +4° C.). The obtained plasma was divided into two aliquots, placed into pre-chilled cryovials and in a freezer at −70° C. until analysis.

Toxicokinetic Calculations Plasma toxicokinetic analyses for melflufen-d5 (III), melflufen and their metabolites, desethyl-melflufen and melphalan were performed according to standard non-compartmental approach using Phoenix WinNonlin system (v. 6.3, Certara Company, USA).

After administration, $C_{max}$, maximum concentration, and $T_{max}$, time at which the maximum concentration was achieved, were read as the coordinates of the highest plasma concentration of the time course. $C_{last}$, last detectable concentration, and $T_{last}$, time of the last detectable concentration, were reported as parameters.

The area under plasma concentration vs. time curve up to the last detectable concentration, $AUC_{last}$, was calculated by the linear trapezoidal rule.

When feasible, the following parameters were calculated:

$t_{1/2,z}$, the half-life of the terminal phase, was calculated by linear regression analysis of the natural-log concentration vs. time curve according to the formula:

$$t_{1/2,z} = \frac{\ln(2)}{\lambda_z}$$

where $-\lambda_z$ is the slope of the regression line. The estimate of $t_{1/2,z}$ was carried out on at least three time points.

$AUC_\infty$ the area under plasma concentration vs. time curve up to infinite time, was calculated by adding the portion of the area calculated as $C_{last}/\lambda_z$ to $AUC_{last}$ assuming mono-exponential decay.

The fraction of $AUC_\infty$ accounted for by the extrapolated area under the curve was calculated as follows:

$$\% \, AUCExtr = 100 \cdot \frac{AUC_{last-\infty}}{AUC_\infty}$$

Individual and descriptive statistics (mean±SD, % CV) plasma concentrations and toxicokinetic parameters were reported with three significant digits.

(iii) Results

No melflufen-d5 (III), melflufen and their metabolites desethyl-melflufen and melphalan were measured in plasma samples of the control group (group 1) as well as in the pre-dose samples of the treated groups 2, 3 and 4.

Systemic exposure parameters on males and females of melflufen-d5 (III), melflufen and their metabolites desethyl-melflufen and melphalan were comparable, therefore descriptive statistics on combined male and female parameters were also reported.

Melflufen-d5 (III)

Summary toxicokinetic parameters of melflufen-d5 (III) are reported in Tables 1 and 2:

TABLE 1

| | | | Melflufen-d5 (III) | | | |
|---|---|---|---|---|---|---|
| Group | Sex | | Tmax (h) | Cmax (µmol/L) | Tlast (h) | AUClast (h*µmol/L) |
| 2 | M | Mean | 0.250 | 0.0977 | 0.556 | 0.0377 |
| | | SD | 0.00 | 0.0339 | 0.0964 | 0.0137 |
| | | CV % | 0.00 | 34.7 | 17.4 | 36.4 |
| 2 | F | Mean | 0.500 | 0.0993 | 0.50 | 0.0296 |
| | | SD | 0.00 | 0.0326 | 0.00 | 0.00925 |
| | | CV % | 0.00 | 32.8 | 0.00 | 31.3 |
| 3 | M | Mean | 0.417 | 0.346 | 0.611 | 0.124 |
| | | SD | 0.144 | 0.107 | 0.0964 | 0.0497 |
| | | CV % | 34.6 | 31.0 | 15.8 | 40.1 |
| 3 | F | Mean | 0.333 | 0.159 | 0.611 | 0.0564 |
| | | SD | 0.144 | 0.0271 | 0.0964 | 0.021 |
| | | CV % | 43.3 | 17.1 | 15.8 | 37.2 |

TABLE 2

| | | | Melflufen-d5 (III) | | | |
|---|---|---|---|---|---|---|
| Group | Sex | | Tmax (h) | Cmax (µmol/L) | Tlast (h) | AUClast (h*µmol/L) |
| 2 | M + F | Mean | 0.375 | 0.0985 | 0.528 | 0.0336 |
| | | SD | 0.137 | 0.0297 | 0.0682 | 0.0114 |
| | | CV % | 36.5 | 30.2 | 12.9 | 33.9 |
| 3 | M + F | Mean | 0.375 | 0.253 | 0.611 | 0.0902 |
| | | SD | 0.137 | 0.124 | 0.0862 | 0.0503 |
| | | CV % | 36.5 | 49.3 | 14.1 | 55.8 |

Melflufen-d5 (III) infused for 30 minutes at the doses of 1.25 and 2.5 mg/kg (groups 2 and 3) reached its maximal plasma concentration at mid-end infusion and then disappeared within 40 minutes from start of dosing. Due to insufficient number of time points on the terminal phase, the half-life was not calculated.

The exposure to melflufen-d5 (III) increased with the dose in terms of peak and area under the curve (2.7-fold versus a 2-fold dose increase, calculated on combined gender parameters).

Mean+SD plasma concentrations of melflufen-d5 (III) after 1.25 and 2.5 mg/kg are show in FIG. 1.

Melflufen Summary toxicokinetic parameters of melflufen are reported in the following Tables 3 and 4:

TABLE 3

| | | | Melflufen | | | |
|---|---|---|---|---|---|---|
| Group | Sex | | Tmax (h) | Cmax (µmol/L) | Tlast (h) | AUClast (h*µmol/L) |
| 4 | M | Mean | 0.250 | 0.124 | 0.500 | 0.0326 |
| | | SD | 0.00 | 0.0469 | 0.00 | 0.0112 |
| | | CV % | 0.00 | 37.7 | 0.00 | 34.4 |
| 4 | F | Mean | 0.417 | 0.163 | 0.500 | 0.0539 |
| | | SD | 0.144 | 0.0812 | 0.00 | 0.0319 |
| | | CV % | 34.6 | 49.8 | 0.00 | 59.2 |

TABLE 4

| | | | Melflufen | | | |
|---|---|---|---|---|---|---|
| Group | Sex | | Tmax (h) | Cmax (µmol/L) | Tlast (h) | AUClast (h*µmol/L) |
| 4 | M + F | Mean | 0.333 | 0.144 | 0.500 | 0.0433 |
| | | SD | 0.129 | 0.063 | 0.00 | 0.0244 |
| | | CV % | 38.7 | 43.8 | 0.00 | 56.4 |

Similar to melflufen-d5 (III), a peak at 15-30 minutes and a rapid disappearance from plasma characterized the kinetics of melflufen infused for 30 minutes at the dose of 2.5 mg/kg (group 4).

Comparison Between Systemic Exposure to Melflufen-d5 (III) and Melflufen

Figure 2:
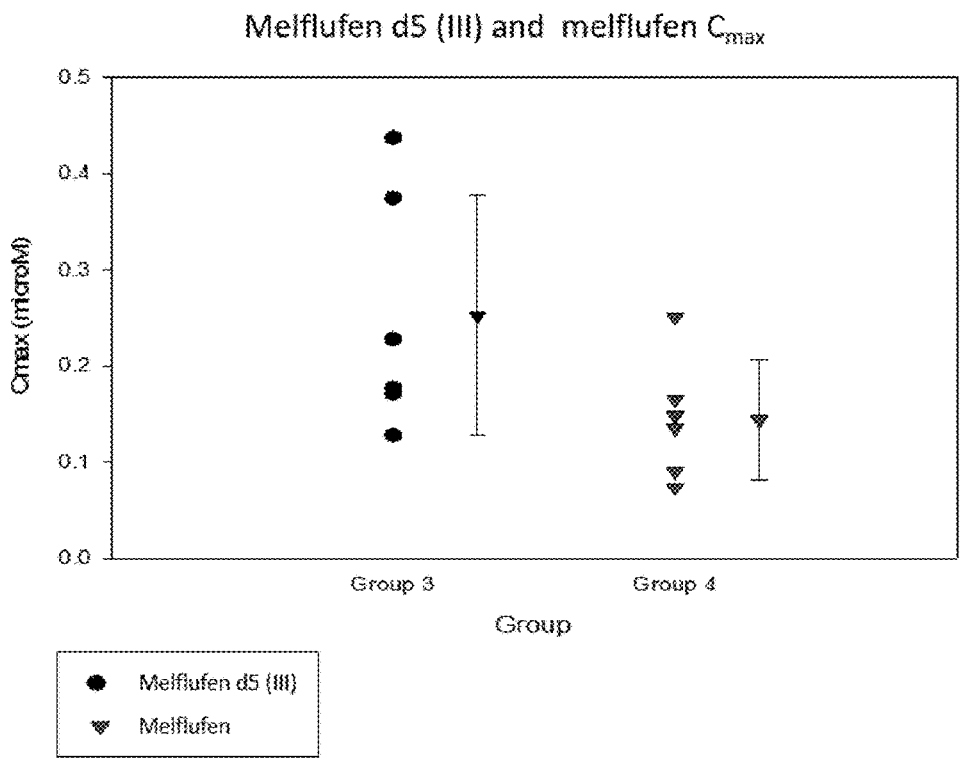
FIG. 2 shows a comparison of individual and mean (±SD) C. of melflufen-d5 (III) or melflufen after administration of melflufen-d5 (III) (group 3, 2.5 mg/kg) or melflufen (group 4, 2.5 mg/kg) to male and female beagle dogs.
Figure 3:
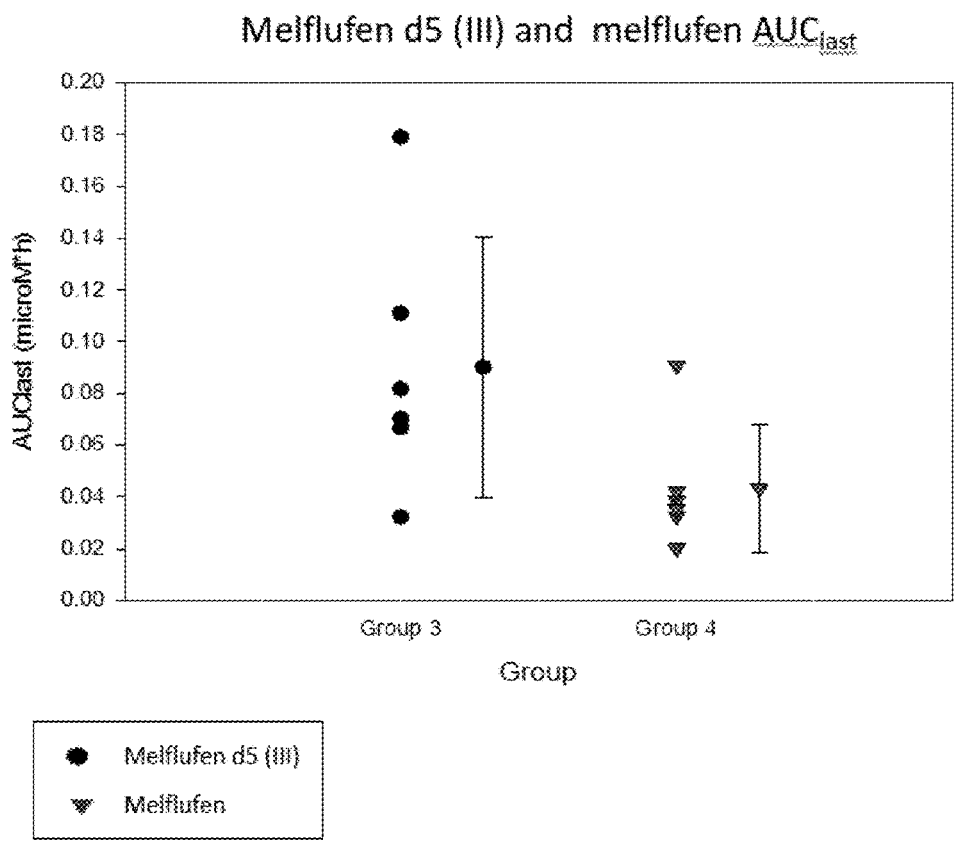
FIG. 3 shows a comparison of individual and mean (±SD) AUCiast of melflufen-d5 (III) or melflufen after administration of melflufen-d5 (III) (group 3, 2.5 mg/kg) or melflufen (group 4, 2.5 mg/kg) to male and female beagle dogs.

Comparison of individual and mean (±SD) systemic exposure parameters of melflufen-d5 (III) (group 3, 2.5 mg/kg) and melflufen (group 4, 2.5 mg/kg) in combined male and female beagle dogs is shown in FIG. 2 (C.) and FIG. 3 (AUC$_{last}$).

The average exposure to melflufen was 2 fold lower than that to melflufen-d5 (III) at 2.5 mg/kg. As shown in the FIGS. 2 and 3, the difference for the mean values was in part driven by the high concentrations measured in one male dog treated with melflufen-d5 (III). However, as can be seen from FIG. 2 and FIG. 3, which show the individual C$_{max}$ and AUC$_{last}$ values for each animal, there is a clear trend of increased C$_{max}$ and increased AUC$_{last}$ for melflufen-d5 (III) compared to melflufen.

The inter-animal variability (CV %) in the two groups was of the same order of magnitude.

Desethyl-Melflufen

Summary toxicokinetic parameters of the metabolite desethyl-melflufen are reported in the Tables 5 and 6:

TABLE 5

| | | | Desethyl-melflufen | | | |
|---|---|---|---|---|---|---|
| Group | Sex | | Tmax (h) | Cmax (µmol/L) | Tlast (h) | AUClast (h*µmol/L) |
| 2 | M | Mean | 0.500 | 0.0356 | 0.667 | 0.0155 |
| | | SD | 0.00 | 0.00678 | 0.00 | 0.00334 |
| | | CV % | 0.00 | 19.0 | 0.00 | 21.5 |
| 2 | F | Mean | 0.500 | 0.0308 | 0.667 | 0.0132 |
| | | SD | 0.00 | 0.00123 | 0.00 | 0.00108 |
| | | CV % | 0.00 | 3.98 | 0.00 | 8.15 |
| 3 | M | Mean | 0.417 | 0.134 | 1.00 | 0.0655 |
| | | SD | 0.144 | 0.0703 | 0.00 | 0.0364 |
| | | CV % | 34.6 | 52.4 | 0.00 | 55.6 |
| 3 | F | Mean | 0.50 | 0.0703 | 1.00 | 0.0358 |
| | | SD | 0.00 | 0.0063 | 0.00 | 0.0035 |
| | | CV % | 0.00 | 8.96 | 0.00 | 9.78 |

TABLE 5-continued

| Group | Sex | | Tmax (h) | Desethyl-melflufen Cmax (μmol/L) | Tlast (h) | AUClast (h*μmol/L) |
|---|---|---|---|---|---|---|
| 4 | M | Mean | 0.50 | 0.0822 | 1.00 | 0.0363 |
|   |   | SD | 0.00 | 0.034 | 0.00 | 0.0143 |
|   |   | CV % | 0.00 | 41.3 | 0.00 | 39.4 |
| 4 | F | Mean | 0.417 | 0.0605 | 0.889 | 0.0287 |
|   |   | SD | 0.144 | 0.00317 | 0.192 | 0.00592 |
|   |   | CV % | 34.6 | 5.24 | 21.6 | 20.6 |

TABLE 6

| Group | Sex | | Tmax (h) | Desethyl-melflufen Cmax (μmol/L) | Tlast (h) | AUClast (h*μmol/L) |
|---|---|---|---|---|---|---|
| 2 | M + F | Mean | 0.500 | 0.0332 | 0.667 | 0.0144 |
|   |   | SD | 0.00 | 0.0051 | 0.00 | 0.00256 |
|   |   | CV % | 0.00 | 15.4 | 0.00 | 17.8 |
| 3 | M + F | Mean | 0.458 | 0.102 | 1.00 | 0.0506 |
|   |   | SD | 0.102 | 0.0567 | 0.00 | 0.0283 |
|   |   | CV % | 22.3 | 55.5 | 0.00 | 55.8 |
| 4 | M + F | Mean | 0.458 | 0.0714 | 0.945 | 0.0325 |
|   |   | SD | 0.102 | 0.0246 | 0.136 | 0.0106 |
|   |   | CV % | 22.3 | 34.5 | 14.4 | 32.7 |

After 1.25 and 2.5 mg/kg melflufen-d5 (III) infusion (groups 2 and 3), the metabolite desethyl-melflufen appeared in plasma at the first sampling time, reaching its maximal concentration at 15-30 minutes to be no longer detectable after 40-60 minutes post-dosing (1.25-2.5 mg/kg). The half-life, estimable in one animal only at the dose of 2.5 mg/kg, was 5 minutes.

The exposure to desethyl-melflufen increased by 3.1-fold on C. and by 3.5-fold on AUCiast vs a 2-fold melflufen-d5 (III) dose increase (calculated on combined gender parameters).

After melflufen administration (group 4), the plasma profile of desethyl-melflufen was similar to that observed after melflufen-d5 (III) administration in terms of $t_{max}$ and $t_{last}$. The half-life, estimable in one animal only at the dose of 2.5 mg/kg, was 7 minutes.

Figure 4:
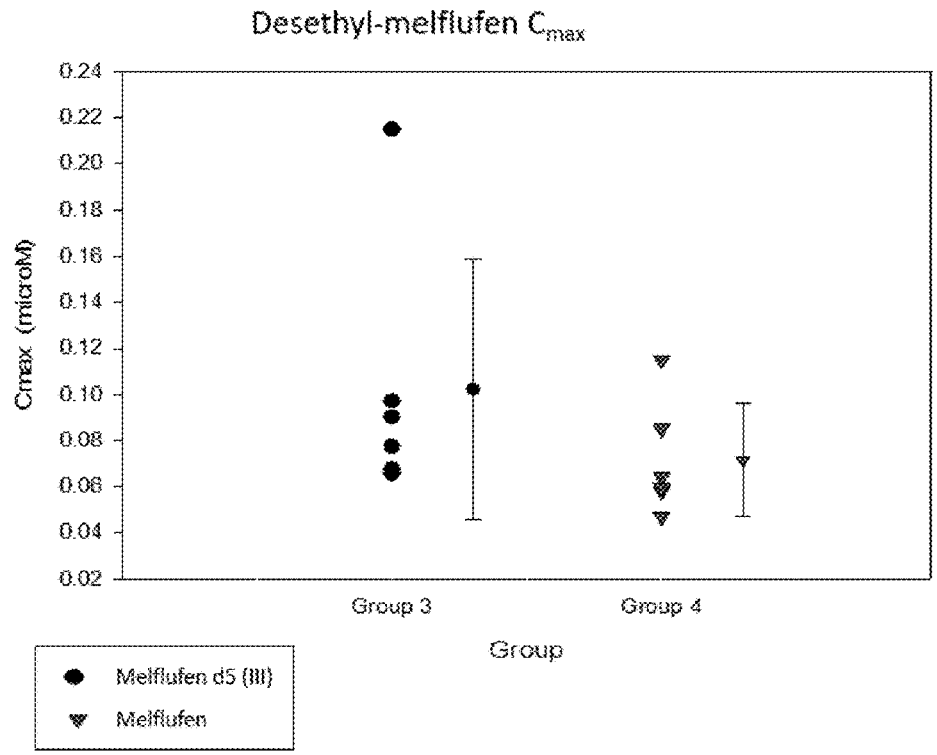
FIG. 4 shows a comparison of individual and mean (±SD) C. of desethyl-melflufen after infusion of melflufen-d5 (III) (group 3, 2.5 mg/kg) and melflufen (group 4, 2.5 mg/kg) to male and female beagle dogs.
Figure 5:
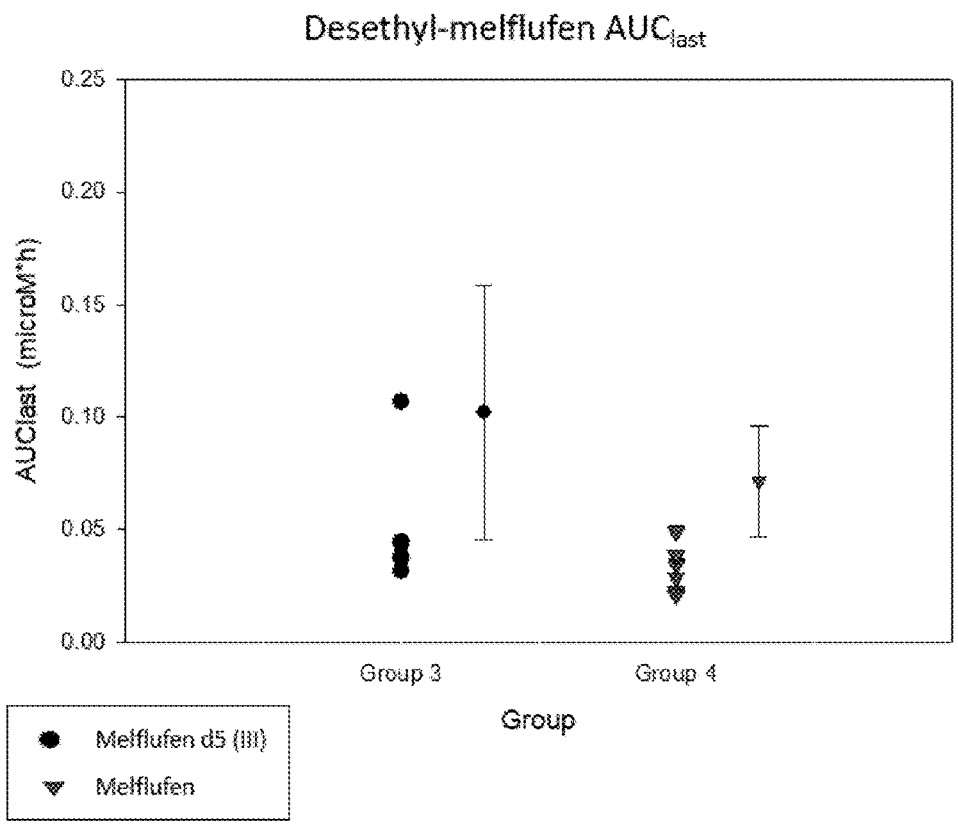
FIG. 5 shows a comparison of individual and mean (±SD) AUCiast of desethyl-melflufen after infusion of melflufen-d5 (III) (group 3, 2.5 mg/kg) and melflufen (group 4, 2.5 mg/kg) to male and female beagle dogs.

Comparison between systemic exposure to desethyl-melflufen after administration of melflufen-d5 (III) or melflufen Comparison of individual and mean (±SD) systemic exposure parameters of desethyl-melflufen after infusion of melflufen-d5 (III) (group 3, 2.5 mg/kg) and melflufen (group 4, 2.5 mg/kg) in combined male and female beagle dogs beagle dogs is shown in FIG. 4 ($C_{max}$) and FIG. 5 (AUC$_{last}$).

The average exposure to desethyl-melflufen was lower after infusion of melflufen at 2.5 mg/kg than after infusion of melflufen-d5 (III) at 2.5 mg/kg. As shown in the FIGS. 4 and 5, the difference for the mean values was mainly driven by the high concentrations of desethyl-melflufen measured in one male dog treated with melflufen-d5 (III). However, as can be seen from FIG. 4, which shows the individual $C_{max}$ values for each animal, there is a trend of increased $C_{max}$ of desethyl-melflufen after infusion of melflufen-d5 (III) compared to melflufen.

Melphalan

Summary toxicokinetic parameters of the metabolite melphalan are reported in the Tables 7 and 8:

TABLE 7

| Group | Sex | | Tmax (h) | Melphalan Cmax (μmol/L) | Tlast (h) | AUClast (h*μmol/L) | t½, z (h) | AUC∞ (h*μmol/L) |
|---|---|---|---|---|---|---|---|---|
| 2 | M | Mean | 0.556 | 1.33 | 4 | 1.77 | 0.658 | 1.80 |
|   |   | SD | 0.0964 | 0.174 | 0 | 0.295 | 0.071 | 0.312 |
|   |   | CV % | 17.4 | 13.1 | 0 | 16.7 | 10.8 | 17.3 |
| 2 | F | Mean | 0.500 | 1.13 | 4 | 1.44 | 0.654 | 1.47 |
|   |   | SD | 0.00 | 0.0701 | 0 | 0.216 | 0.0186 | 0.221 |
|   |   | CV % | 0.00 | 6.17 | 0 | 15 | 2.84 | 15.1 |
| 3 | M | Mean | 0.500 | 2.93 | 4 | 3.28 | 0.658 | 3.33 |
|   |   | SD | 0.00 | 0.751 | 0 | 0.517 | 0.0203 | 0.522 |
|   |   | CV % | 0.00 | 25.6 | 0 | 15.8 | 3.09 | 15.7 |
| 3 | F | Mean | 0.500 | 2.59 | 4 | 2.99 | 0.587 | 3.03 |
|   |   | SD | 0.00 | 0.286 | 0 | 0.293 | 0.0407 | 0.302 |
|   |   | CV % | 0.00 | 11.0 | 0 | 9.80 | 6.94 | 10.0 |
| 4 | M | Mean | 0.500 | 2.40 | 4 | 2.84 | 0.681 | 2.9 |
|   |   | SD | 0.00 | 0.649 | 0 | 0.0622 | 0.0362 | 0.0534 |
|   |   | CV % | 0.00 | 27.1 | 0 | 2.19 | 5.31 | 1.84 |
| 4 | F | Mean | 0.500 | 2.07 | 4 | 2.61 | 0.626 | 2.64 |
|   |   | SD | 0.00 | 0.565 | 0 | 0.752 | 0.0662 | 0.747 |
|   |   | CV % | 0.00 | 27.3 | 0 | 28.9 | 10.6 | 28.3 |

TABLE 8

| | | | Melphalan | | | | | |
|---|---|---|---|---|---|---|---|---|
| Group | Sex | | Tmax (h) | Cmax (µmol/L) | Tlast (h) | AUClast (h*µmol/L) | $t^{1/2}$, z (h) | AUC∞ (h*µmol/L) |
| 2 | M + F | Mean | 0.528 | 1.23 | 4 | 1.60 | 0.656 | 1.63 |
| | | SD | 0.0682 | 0.161 | 0 | 0.292 | 0.0465 | 0.304 |
| | | CV % | 12.9 | 13 | 0 | 18.2 | 7.09 | 18.6 |
| 3 | M + F | Mean | 0.5 | 2.76 | 4 | 3.13 | 0.622 | 3.18 |
| | | SD | 0 | 0.542 | 0 | 0.408 | 0.0484 | 0.416 |
| | | CV % | 0 | 19.7 | 0 | 13.0 | 7.78 | 13.1 |
| 4 | M + F | Mean | 0.5 | 2.23 | 4 | 2.72 | 0.654 | 2.77 |
| | | SD | 0 | 0.572 | 0 | 0.494 | 0.0563 | 0.495 |
| | | CV % | 0 | 25.6 | 0 | 18.1 | 8.62 | 17.8 |

After 1.25 and 2.5 mg/kg melflufen-d5 (III) infusion, the metabolite melphalan appeared in plasma at the first sampling time, reached its maximal concentration at a mean t. of 30 minutes and was detectable until 4 hours post-dosing after each melflufen-d5 (III) dose. The estimate half-life was approximately 40 minutes.

After melflufen infusion (group 4), the plasma profile of melphalan was comparable to that formed by melflufen-d5 (III). $T_{max}$ and $t_{last}$ of melphalan at the two treatments were similar.

The exposure to melphalan increased with the administered dose of melflufen-d5 (III) in terms of peak and AUC values: by combining genders, a 2-fold dose increase corresponded to a 2.2-fold increase in mean $C_{mas}$ and a 2.0-fold increase in $AUC_{last}$ and $AUC_\infty$ of the metabolite.

At the two ascending doses of melflufen-d5 (III), the melphalan $AUC_{last}$ was 48- and 35-fold higher than melflufen-d5 (III) exposure, respectively (calculated on mean AUCiast values of combined sexes data). At the two ascending doses of melflufen-d5 (III), melphalan AUCiast was on average 51.1-fold (range 37-70) and 44.8-fold (range 22-100) higher than melflufen-d5 (III) exposure, respectively (calculated on individual values of combined sexes).

After melflufen infusion, melphalan AUCiast was on average 75-fold (range 38-142) higher than melflufen exposure (calculated on individual values of combined sexes).

Figure 6A:
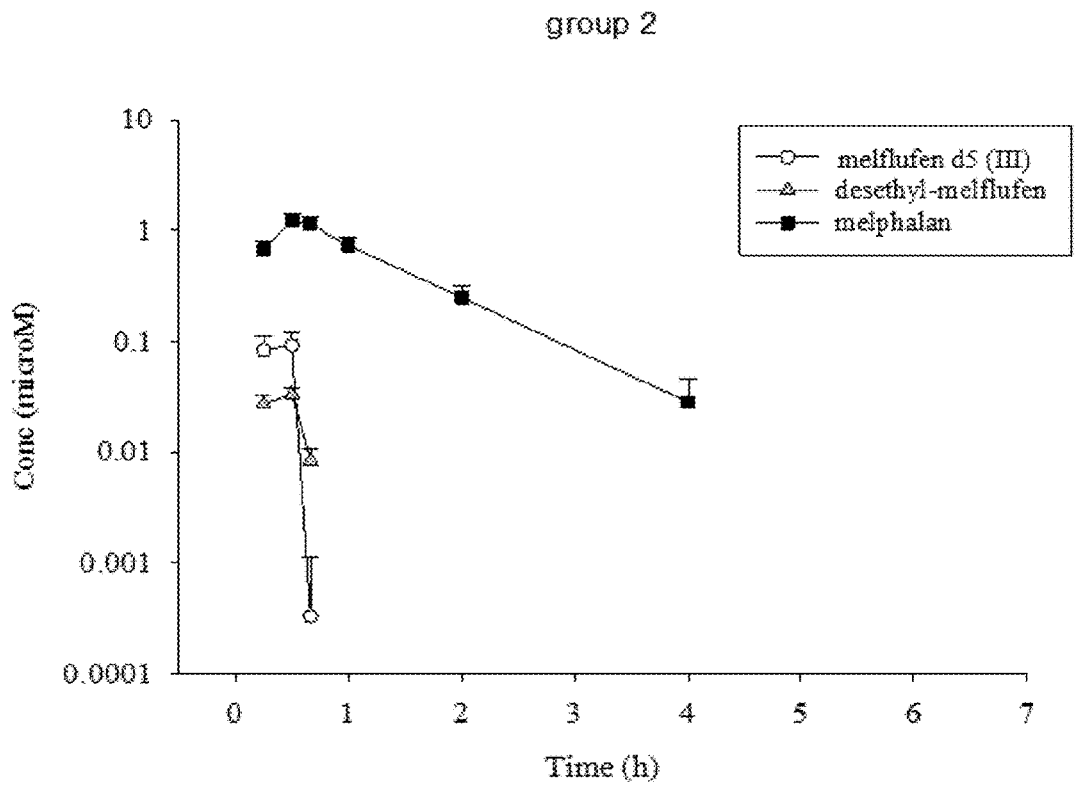
FIGS. 6a and 6b show the mean plasma concentrations of melflufen-d5 (III) and its metabolites desethyl-melflufen and melphalan after infusion of 1.25 mg/kg melflufen-d5 (III) to male and female beagle dogs (group 2 combined sexes).
Figure 6B:
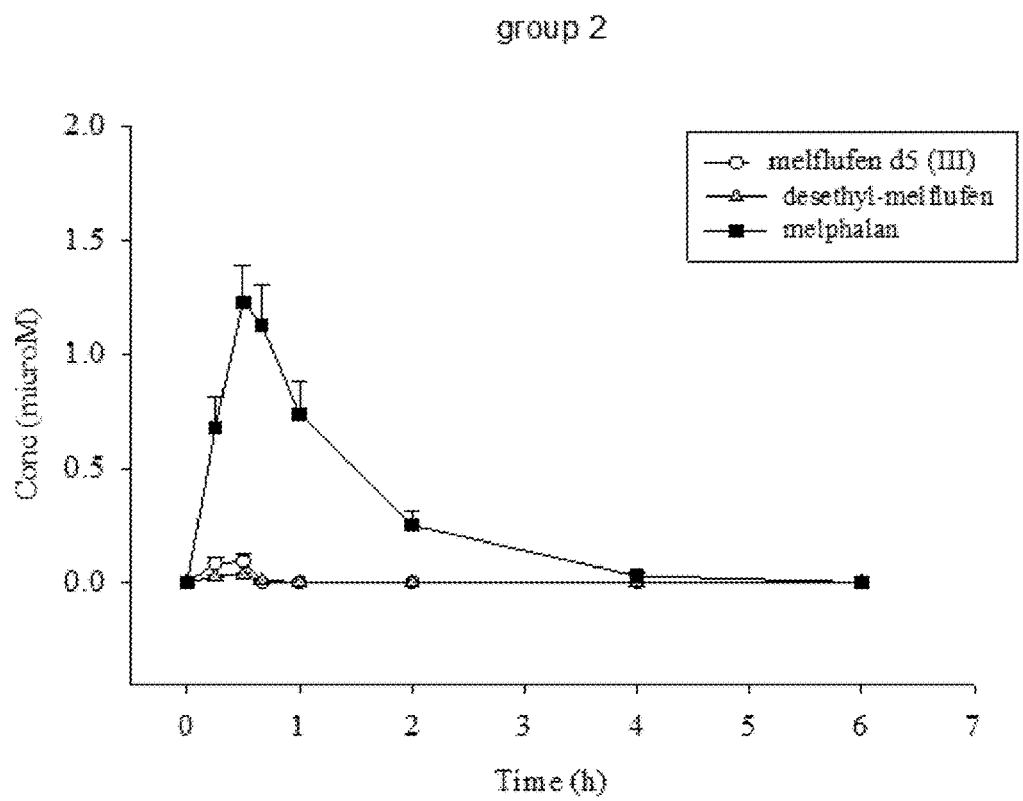
Figure 7A:
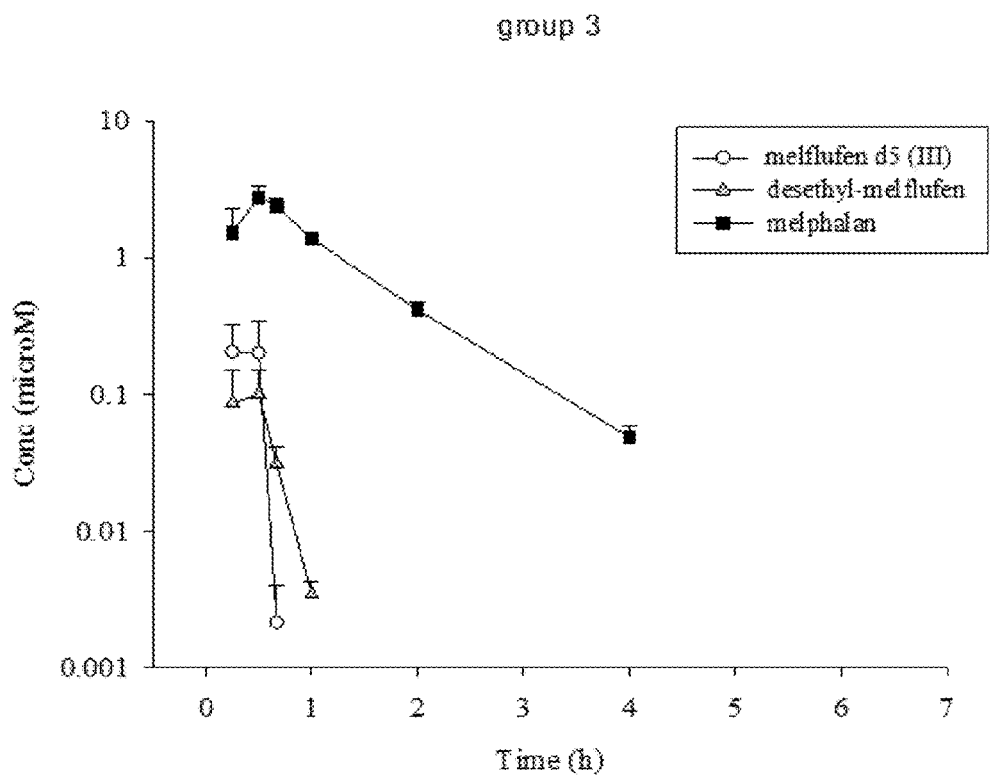
FIGS. 7a and 7b show the mean plasma concentrations of melflufen-d5 (III) and its metabolites desethyl-melflufen and melphalan after infusion of 2.5 mg/kg melflufen-d5 (III) to male and female beagle dogs (group 3 combined sexes).
Figure 7B:
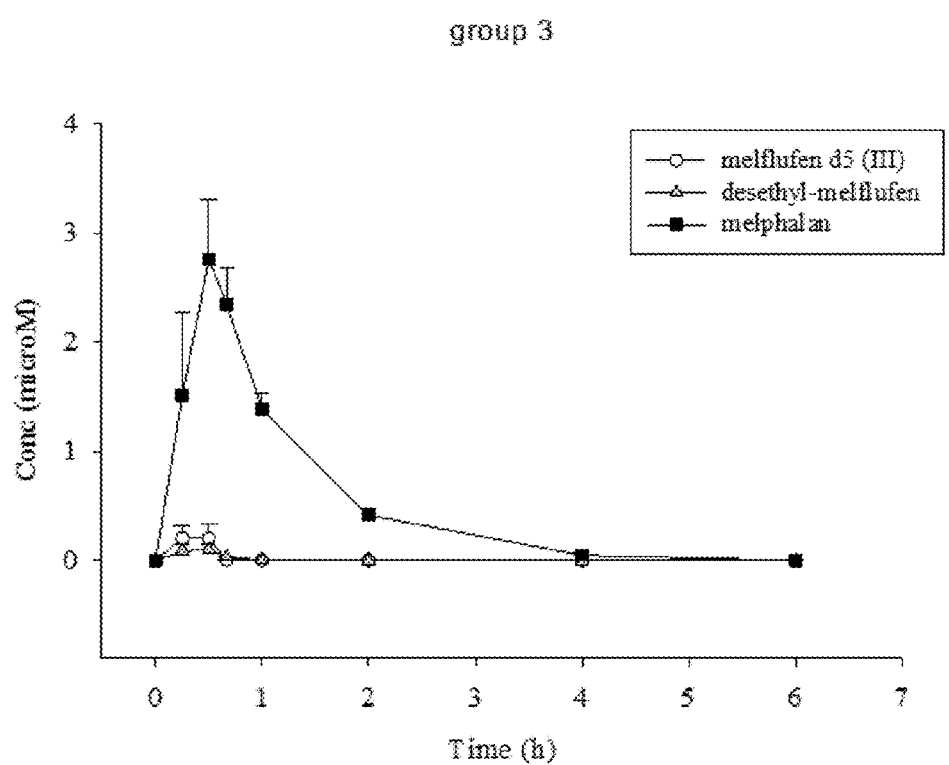

Mean+SD plasma concentrations of melflufen-d5 (III), melphalan and desethyl-melflufen after infusion of melflufen-d5 (III) in dogs (combined sexes) in group 2 or group 3 are shown in the FIGS. 6a (group 2, logarithmic scale) and 6b (group 2, non-logarithmic scale) and FIGS. 7a (group 3, logarithmic scale) and 7b (group 3, non-logarithmic scale). As shown in FIGS. 7a and 7b, the mean $C_{max}$ after infusion of 2.5 mg/kg melflufen-d5 (III) was 2.73 µmol/L.

Figure 8A:
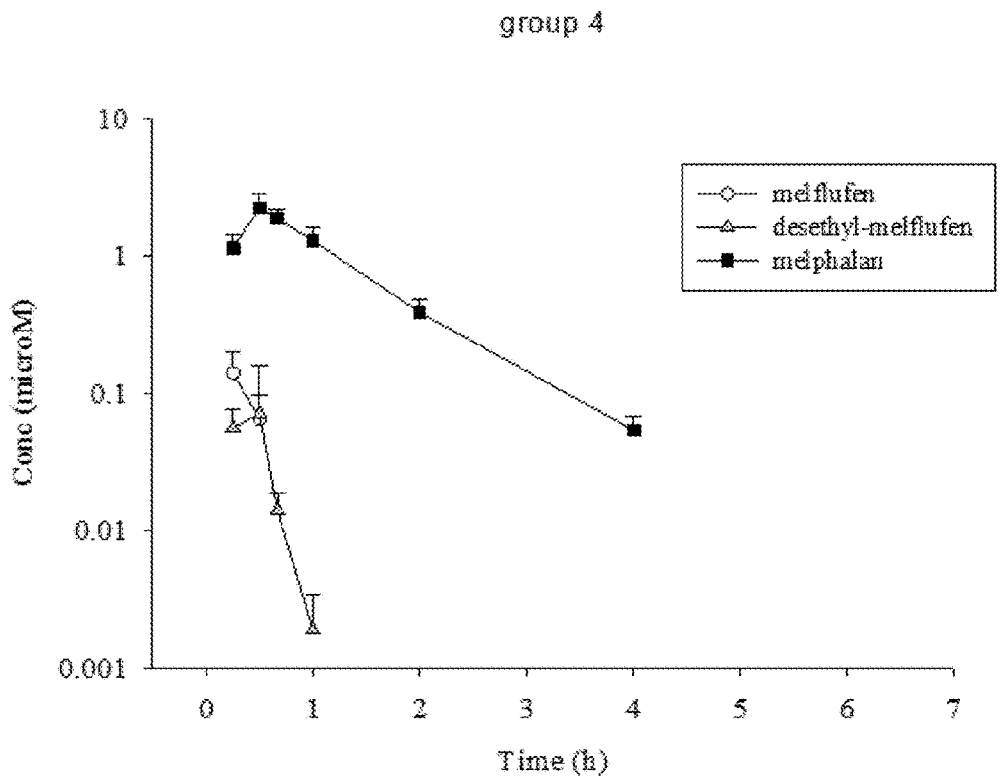
FIGS. 8a and 8b show the mean plasma concentrations of melflufen and its metabolites desethyl-melflufen and melphalan after infusion of 2.5 mg/kg melflufen to male and female beagle dogs (group 4 combined sexes).
Figure 8B:
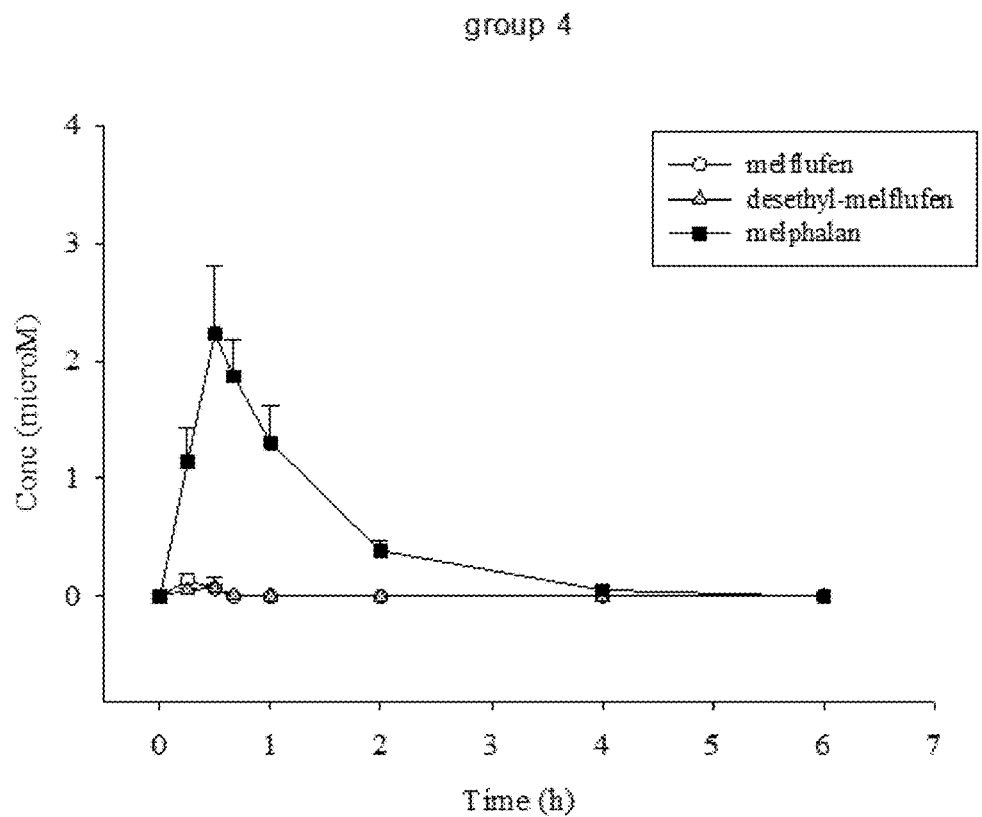

Mean+SD plasma concentrations of melflufen, melphalan and desethyl-melflufen after infusion of melflufen in dogs (combined sexes) in group 4 is shown in the FIGS. 8a (group 4, logarithmic scale) and 8b (group 4, non-logarithmic scale). As shown in FIGS. 8a and 8b, the mean C. after infusion of 2.5 mg/kg melflufen was 2.23 µmon.

Figure 9:
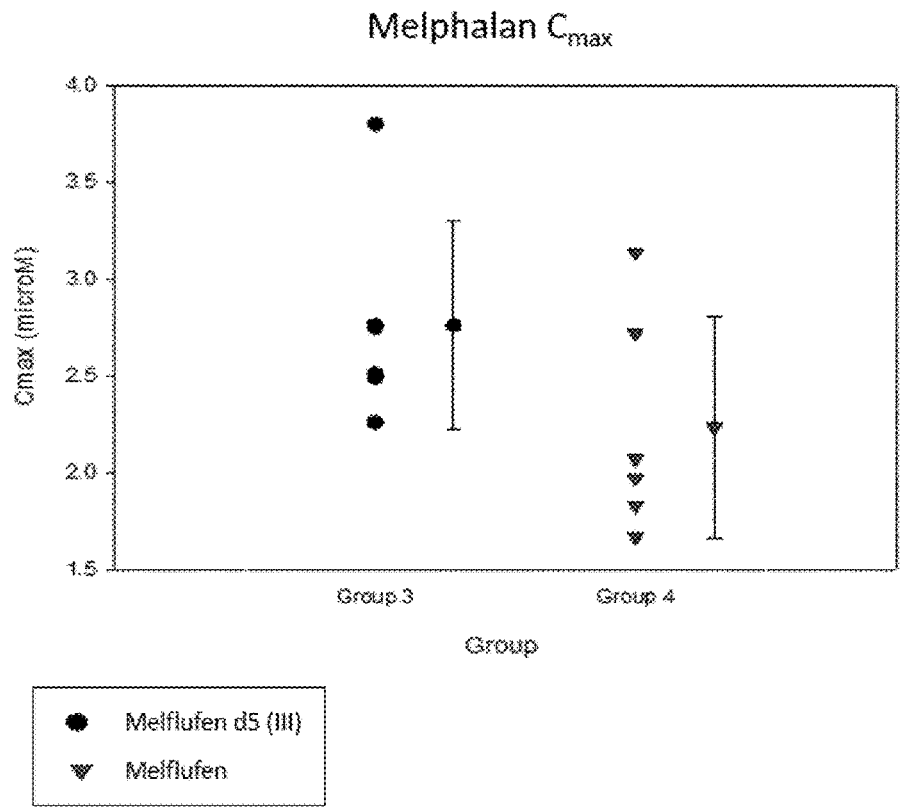
FIG. 9 shows a comparison of individual and mean (±SD) $C_{max}$ of melphalan after infusion of melflufen-d5 (III) (group 3, 2.5 mg/kg) or melflufen (group 4, 2.5 mg/kg) to male and female beagle dogs.
Figure 10:
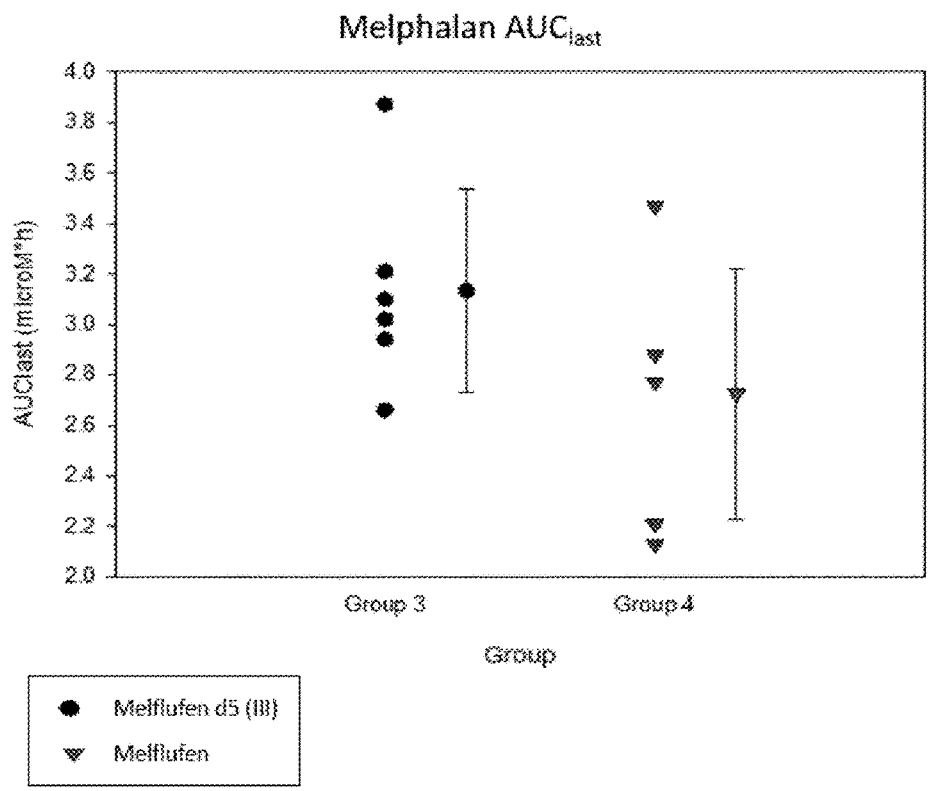
FIG. 10 shows a comparison of individual and mean (±SD) $AUC_{last}$ of melphalan after infusion of melflufen-d5 (III) (group 3, 2.5 mg/kg) or melflufen (group 4, 2.5 mg/kg) to male and female beagle dogs.
Figure 11:
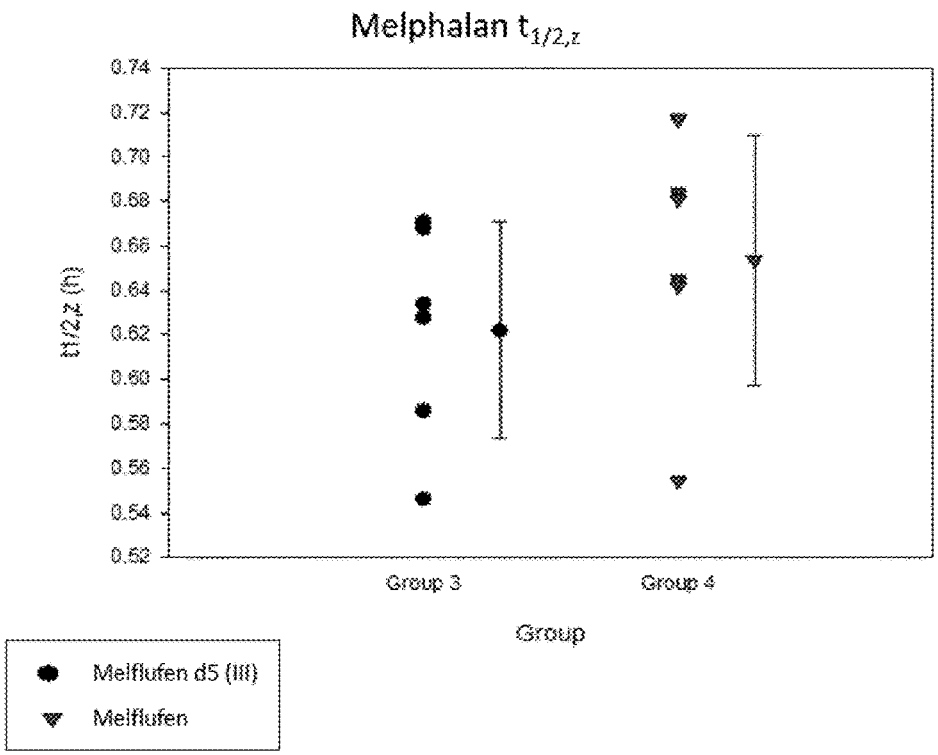
FIG. 11 shows a comparison of individual and mean (±SD) $_{1/2,z}$ of melphalan after infusion of melflufen-d5 (III) (group 3, 2.5 mg/kg) or melflufen (group 4, 2.5 mg/kg) to male and female beagle dogs.
Figure 12:
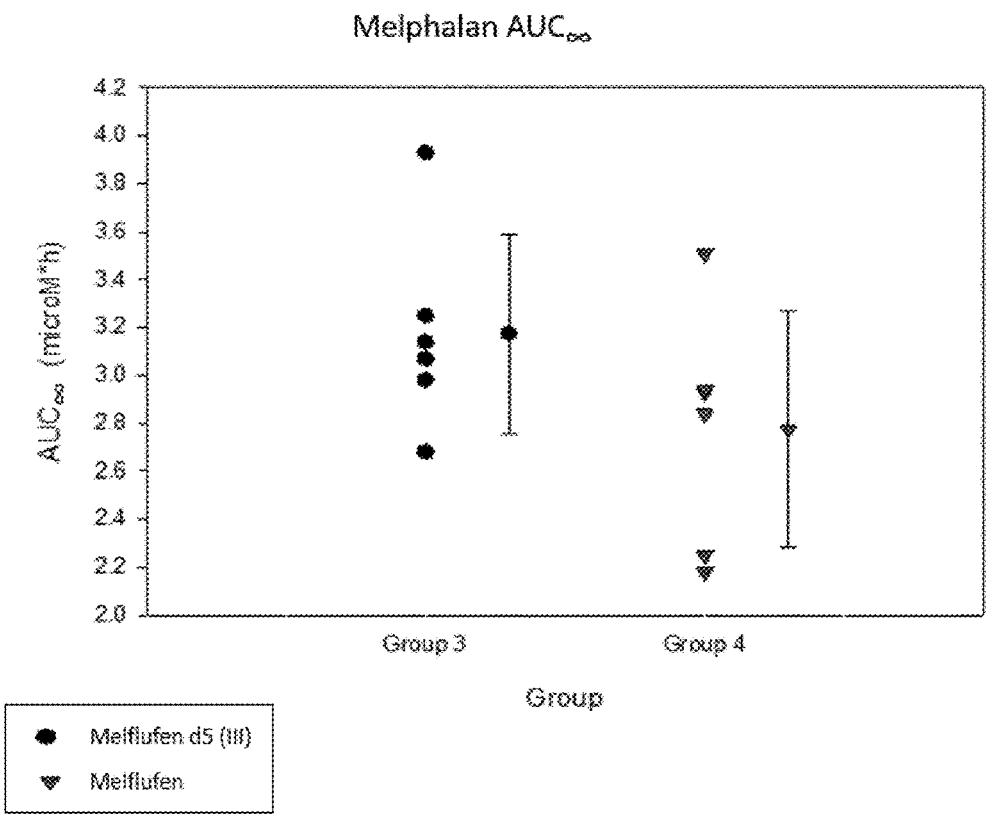
FIG. 12 shows a comparison of individual and mean (±SD) $AUG_{\infty}$ of melphalan after infusion of melflufen-d5 (III) (group 3, 2.5 mg/kg) or melflufen (group 4, 2.5 mg/kg) to male and female beagle dogs.

Comparison Between Systemic Exposure to Melphalan After Administration of Melflufen-d5 (III) or Melflufen Comparison of individual and mean (±SD) systemic exposure parameters of melphalan after infusion of melflufen-d5 (III) (group 3, 2.5 mg/kg) and melflufen (group 4, 2.5 mg/kg) in combined male and female beagle dogs beagle dogs is shown in FIG. 9 ($C_{max}$) and FIG. 10 (AU-$C_{last}$). The $t_{1/2,z}$ and the $AUC_\infty$ results are also shown in FIGS. 11 and 12, respectively.

The average exposure to melphalan was lower after infusion of melflufen at 2.5 mg/kg than after infusion of melflufen-d5 (III) at 2.5 mg/kg. As can be seen from FIGS. 9, 10 and 21, which shows the individual $C_{max}$, $AUC_{last}$ and $AUC_\infty$ values for each animal, there is a trend of increased $C_{max}$, increased $AUC_{last}$ and increased $AUC_\infty$ of melphalan after infusion of melflufen-d5 (III) compared to melflufen. As shown in FIG. 11, the average $t_{1/2,z}$ for melphalan was lower after infusion of melflufen-d5 (III) at 2.5 mg/kg than after infusion of melflufen, and there is a trend of decreased $t_{1/2,z}$ for melphalan in individual animals after infusion of melflufen-d5 (III) compared to melflufen.

Conclusions

Systemic exposure descriptors of melflufen-d5 (III), melflufen and their metabolites desethyl-melflufen and melphalan after single 30 minutes infusion of melflufen-d5 (III) (1.25 and 2.5 mg/kg) or melflufen (2.5 mg/kg) were similar in male and female.

After melflufen-d5 (III) infusion, melflufen-d5 (III) and the metabolite desethy-melflufen disappeared rapidly from the systemic circulation. The exposure to desethyl-melflufen was about one-half of the parent compound exposure.

The metabolite melphalan was rapidly and extensively formed. Melphalan was detected in plasma up to 4 hours after the end of infusion, decaying with a terminal half-life of about 40 minutes. $T_{max}$, $t_{last}$ and $t_{1/2,z}$ of melphalan were constant between melflufen-d5 (III) doses. In combined sexes, the extent of exposure to the formed melphalan was approximately 50-fold higher than melflufen-d5 (III) exposure.

After increasing incremental doses of melflufen-d5 (III) infusion, the systemic exposure increased as expected (melphalan) and slightly more than expected (melflufen-d5 (III) and desethyl-melflufen) assuming dose proportionality.

Comparing equivalent doses of melflufen-d5 (III) and melflufen, overall the exposure to melflufen-d5 (III) and the active metabolite melphalan were consistently higher after infusion of melflufen-d5 (III) compared to melflufen. This increased exposure to melflufen-d5 (III) and melphalan for identical doses of melflufen-d5 (III) and melflufen is a very significant benefit.

The invention claimed is:

1. A compound of formula (I), or a pharmaceutically acceptable salt thereof,

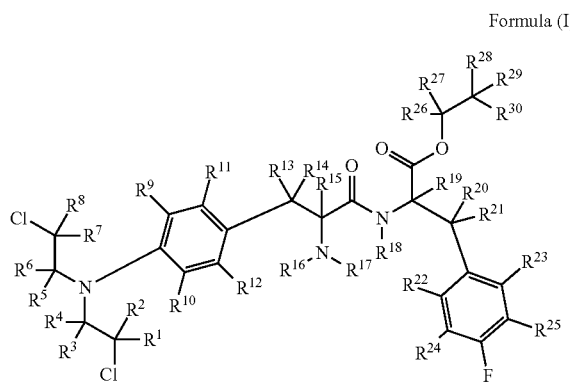

wherein, each $R^9$-$R^{30}$ is independently selected from the group consisting of H and deuterium, and at least one of $R^9$-$R^{30}$ is deuterium with an abundance level of at least 1 mol %, 5 mol %, 10 mol %, 50 mol %, 90 mol % or 98 mol % deuterium; and each $R^1$-$R^8$ is H.

2. The compound of claim 1 or a pharmaceutically acceptable salt thereof, wherein at least one of $R^9$-$R^{15}$ is deuterium with an abundance level of at least 5 mol %.

3. The compound of claim 1 or a pharmaceutically acceptable salt thereof, wherein at least one of $R^{16}$-$R^{18}$ is deuterium with an abundance level of at least 5 mol %.

4. The compound of claim 1 or a pharmaceutically acceptable salt thereof, wherein at least one of $R^{19}$-$R^{25}$ is deuterium with an abundance level of at least 5 mol %.

5. The compound of claim 1 or a pharmaceutically acceptable salt thereof, wherein at least one of $R^{26}$-$R^{30}$ is deuterium with an abundance level of at least 5 mol %.

6. The compound of claim 1 or a pharmaceutically acceptable salt thereof, wherein at least two of $R^{26}$-$R^{30}$ is deuterium.

7. The compound of claim 1 or a pharmaceutically acceptable salt thereof, wherein the abundance level is at least 10 mol %, 50 mol %, 90 mol % or 98 mol % deuterium.

8. The compound of claim 1 or a pharmaceutically acceptable salt thereof, wherein the compound has a structural formula according to:

9. The compound of claim 1 or a pharmaceutically acceptable salt thereof, wherein the compound has a structural formula according to:

10. The compound of claim 1 or a pharmaceutically acceptable salt thereof, wherein the compound has a structural formula selected from the group consisting of:

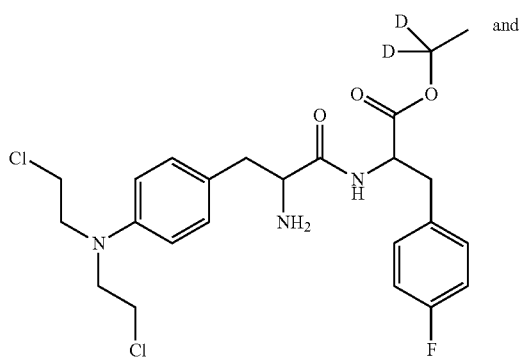

and

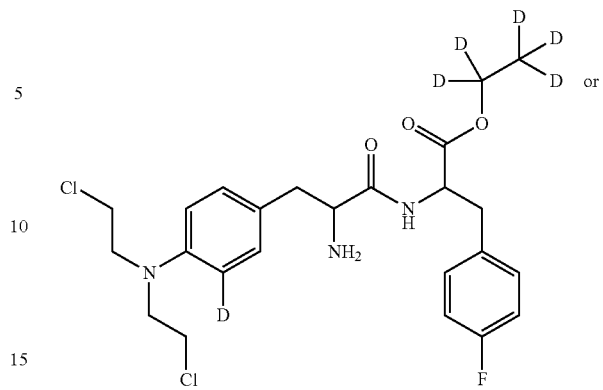

or

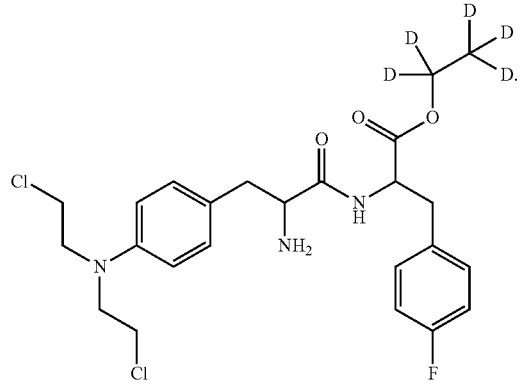

11. The compound of claim 1 or a pharmaceutically acceptable salt thereof, wherein the compound has a structural formula according to:

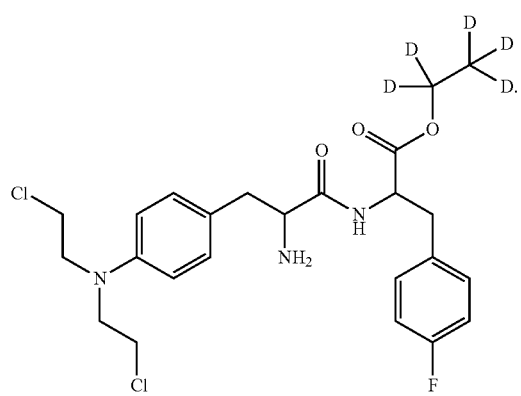

12. The compound of claim 1 or a pharmaceutically acceptable salt thereof, wherein the compound has a structural formula according to:

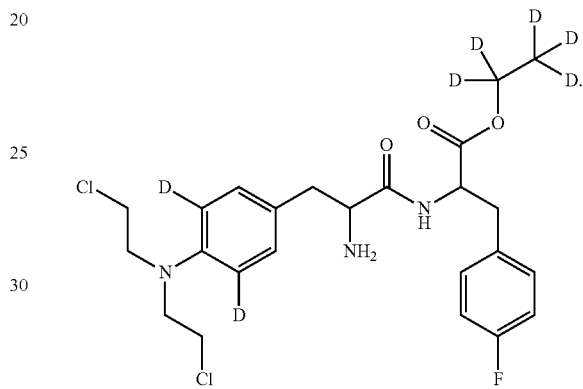

13. A pharmaceutical composition comprising the compound of claim 1 or a pharmaceutically acceptable salt thereof, together with a pharmaceutically acceptable carrier.

14. The pharmaceutical composition of claim 13, which further comprises a protease inhibitor (PI), an immunomodulatory drug (IMiD) or an alkylator.

15. The compound of claim 1, or a pharmaceutically acceptable salt thereof, having a structure of formula (Ia):

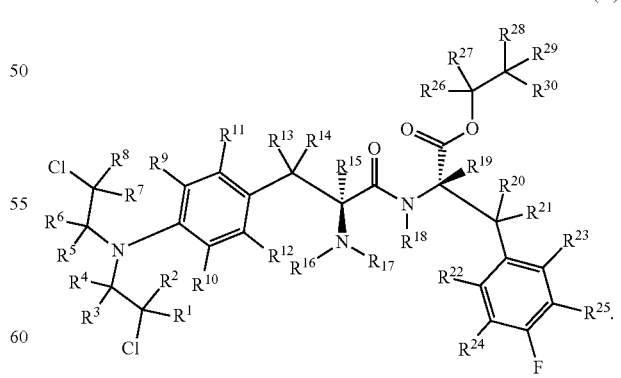

(Ia)

16. The compound of claim 1, wherein the compound is ($^2$H$_5$) ethyl (2S)-2-[(2S)-2-amino-3-{4-[bis (2-chloroethyl) amino] phenyl} propanamido]-3-(4-fluorophenyl) propanoate hydrochloride.

17. A compound having a structural formula according to:
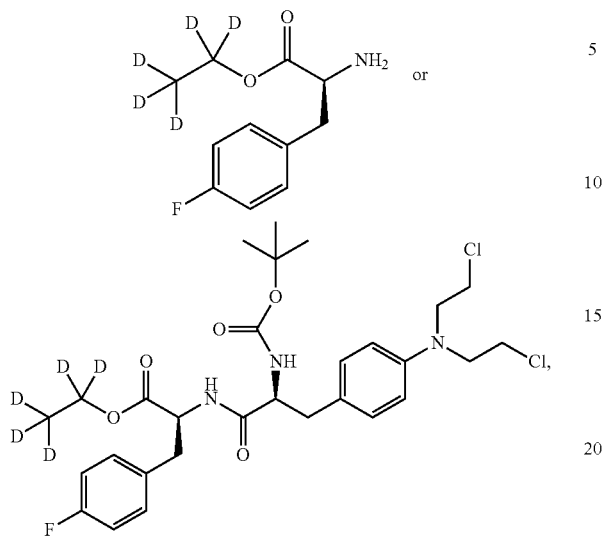
or a pharmaceutically acceptable salt thereof.
* * * * *